(12) United States Patent
Daughton et al.

(10) Patent No.: US 10,973,469 B2
(45) Date of Patent: Apr. 13, 2021

(54) MAPPING OF BREAST ARTERIAL CALCIFICATIONS

(71) Applicant: CureMetrix, Inc., La Jolla, CA (US)

(72) Inventors: William Scott Daughton, Los Alamos, NM (US); Hoanh X Vu, Huntington Beach, CA (US); Homayoun Karimabadi, Del Mar, CA (US)

( * ) Notice: Subject to any disclaimer, the term of this patent is extended or adjusted under 35 U.S.C. 154(b) by 101 days.

(21) Appl. No.: 16/336,047

(22) PCT Filed: Sep. 22, 2017

(86) PCT No.: PCT/US2017/053093
§ 371 (c)(1),
(2) Date: Mar. 22, 2019

(87) PCT Pub. No.: WO2018/057984
PCT Pub. Date: Mar. 29, 2018

(65) Prior Publication Data
US 2019/0223809 A1    Jul. 25, 2019

Related U.S. Application Data

(60) Provisional application No. 62/482,177, filed on Apr. 5, 2017, provisional application No. 62/399,209, filed on Sep. 23, 2016.

(51) Int. Cl.
*A61B 5/00* (2006.01)
*G06T 5/00* (2006.01)
(Continued)

(52) U.S. Cl.
CPC .............. *A61B 5/7275* (2013.01); *A61B 6/12* (2013.01); *A61B 6/502* (2013.01); *A61B 6/5205* (2013.01);
(Continued)

(58) Field of Classification Search
None
See application file for complete search history.

(56) References Cited

U.S. PATENT DOCUMENTS

| | | | |
|---|---|---|---|
| 5,757,953 A * | 5/1998 | Jang ...................... | G06K 9/342 382/132 |
| 2005/0027188 A1* | 2/2005 | Metaxas ................ | A61B 5/055 600/410 |

(Continued)

OTHER PUBLICATIONS

Cheng et al. "Automated Delineation of Calcified Vessels in Mammography by Tracking With Uncertainty and Graphical linking Techniques." In: IEEE Transactions on Medical 165, 169-216, 220-255 A Imaging, vol. 31, No. 11, Nov. 2012 [online] [retrieved on Nov. 28, 2017 (Nov. 28, 2017)] Retrieved from the Internet , 13-15, 64-66, 115-117, entire document, especially Abstract; p. 2-8, 12.

(Continued)

*Primary Examiner* — Kim Y Vu
*Assistant Examiner* — Nathan J Bloom
(74) *Attorney, Agent, or Firm* — Torrey Pines Law Group, PC

(57) ABSTRACT

A method includes receiving an image from a mammogram, removing noise from the image, computing a point of interest on the de-noised image, creating a mesoscale region of interest on the de-noised image, computing a connectivity for the mesoscale region of interest, identifying a connected component using the computed connectivity, where the connected component represents a branch of a global curvilinear structure, selecting a set of branches based on a physical property for each branch of the global curvilinear structure, pruning each branch based on an error-tolerant, adaptive polynomial fit, identifying remaining regions of interest in each pruned branch, and growing a chain formed by remaining points of interest included in the remaining
(Continued)

regions of interest, where the chain represents a macroscopic, global curvilinear calcified arterial structure. The quantitation of the calcified arterial structures may be used as a biomarker for risk stratification of heart disease.

15 Claims, 20 Drawing Sheets

(51) Int. Cl.
| | |
|---|---|
| *G06K 9/40* | (2006.01) |
| *G06T 7/11* | (2017.01) |
| *G06K 9/34* | (2006.01) |
| *G06K 9/00* | (2006.01) |
| *G06K 9/48* | (2006.01) |
| *G06T 7/00* | (2017.01) |
| *G06K 9/32* | (2006.01) |
| *G06T 7/187* | (2017.01) |
| *G06K 9/52* | (2006.01) |
| *G06T 7/155* | (2017.01) |
| *G16H 30/40* | (2018.01) |
| *A61B 6/12* | (2006.01) |
| *A61B 6/00* | (2006.01) |
| *G06K 9/62* | (2006.01) |

(52) U.S. Cl.
CPC ....... *G06K 9/00127* (2013.01); *G06K 9/3233* (2013.01); *G06K 9/3241* (2013.01); *G06K 9/342* (2013.01); *G06K 9/40* (2013.01); *G06K 9/48* (2013.01); *G06K 9/525* (2013.01); *G06K 9/6219* (2013.01); *G06K 9/6251* (2013.01); *G06T 5/002* (2013.01); *G06T 7/0012* (2013.01); *G06T 7/11* (2017.01); *G06T 7/155* (2017.01); *G06T 7/187* (2017.01); *G16H 30/40* (2018.01); *G06K 2209/051* (2013.01); *G06T 2207/10116* (2013.01); *G06T 2207/20036* (2013.01); *G06T 2207/20064* (2013.01); *G06T 2207/20182* (2013.01); *G06T 2207/30068* (2013.01); *G06T 2207/30101* (2013.01)

(56) References Cited

U.S. PATENT DOCUMENTS

| | | |
|---|---|---|
| 2006/0013460 A1 | 1/2006 | Dehmeshki |
| 2007/0047787 A1* | 3/2007 | Oakley ................ G06T 7/0012 382/128 |
| 2008/0187199 A1* | 8/2008 | Gulsun .................. G06T 7/149 382/131 |
| 2010/0166283 A1* | 7/2010 | Grosskopf ............. G06T 7/149 382/131 |
| 2010/0215238 A1 | 8/2010 | Lu et al. |
| 2014/0210821 A1 | 7/2014 | Kapoor et al. |
| 2014/0363064 A1* | 12/2014 | Lee ........................ G06K 9/62 382/128 |
| 2015/0010219 A1 | 1/2015 | Behiels |
| 2016/0063699 A1 | 3/2016 | Gustafson |
| 2017/0148158 A1* | 5/2017 | Najarian .............. A61B 5/7203 |
| 2020/0051246 A1* | 2/2020 | Carmi .................. G06T 11/001 |

OTHER PUBLICATIONS

International Search Report and Written Opinion dated Jan. 2, 2018 for PCT/US17/53093, 16 pages.

Molloi et al. "Quantification of breast arterial calcification using full field digital Mammography." 154-255 In: Med Phys. Apr. 2008,35(4):1428-39 [online] [retrieved on Nov. 28, 2017 (Nov. 28, 2017)) RetrievP.ri from the Internet—:URL: https://www.nc.bi.1l|111.nih.gov/pubmed/184!:11538>. entire document, especially Abstract; p. 2, col. 2; p. 6, col. 2; p. 8, col. 1-2.

\* cited by examiner

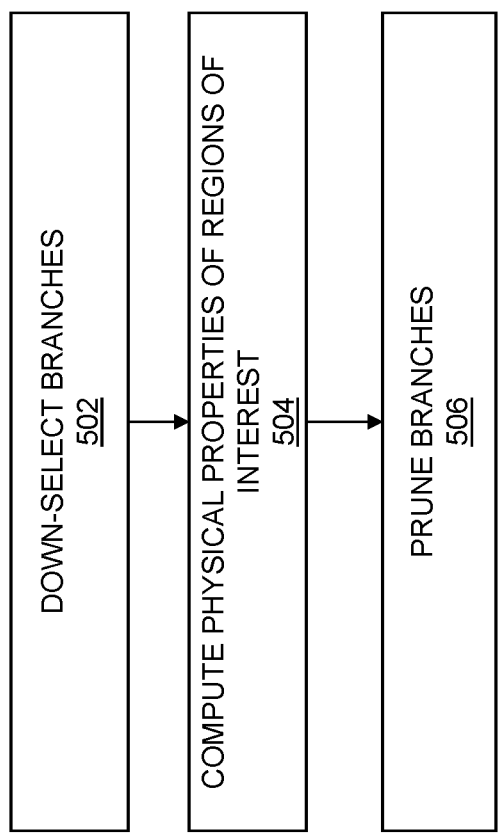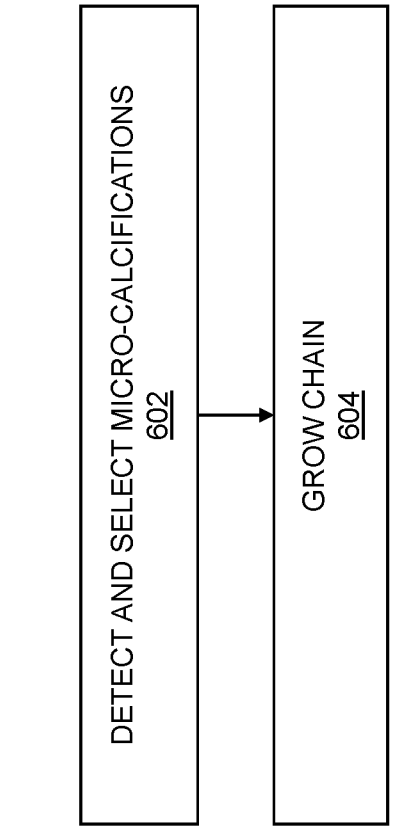

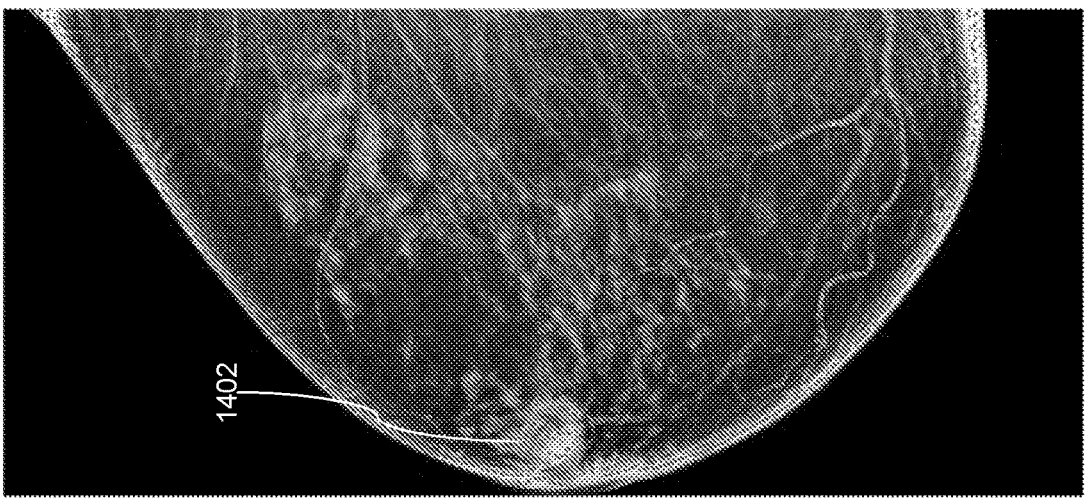

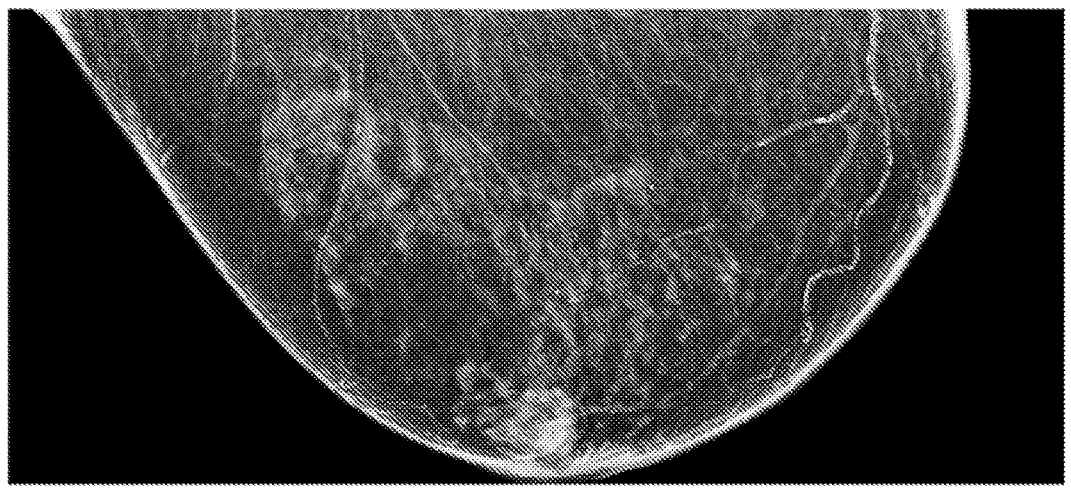

MAPPING OF BREAST ARTERIAL CALCIFICATIONS

CROSS-REFERENCE TO RELATED APPLICATIONS

This application claims priority from U.S. Provisional Application Ser. No. 62/399,209 filed on Sep. 23, 2016, and U.S. Provisional Application Ser. No. 62/482,177 filed on Apr. 5, 2017, each of which is incorporated herein by reference in its entirety.

FIELD

The present disclosure generally relates to devices, systems, and methods for detecting calcifications and for constructing global calcified arterial structures from mammograms, for quantitating the calcified arterial structures and for determining a patient's risk for heart disease.

INTRODUCTION

An analysis of 10 cross-sectional studies has indicated that breast arterial calcification ("BAC") is significantly associated with coronary artery disease (Jiang X. et al., Association of breast arterial calcification with stroke and angiographically proven coronary artery disease: a meta-analysis, *Menopause* 2015, 22(2): 136-43). Further, it has been recently reported that not only is there is a strong quantitative association of BAC with coronary artery calcification but that breast BAC is superior to standard cardiovascular risk factors (Margolies L. et al., Digital Mammography and Screening for Coronary Artery Disease, *JACC Cardiovasc Imaging* 2016, 9(4):350-60).

SUMMARY

Accordingly, the inventors herein have succeeded in devising a new and improved approach for detecting calcifications, constructing global calcified arterial structures from mammograms and for determining a patient's risk for heart disease. Thus, the present invention is directed to methods and to systems and computer program products based upon the methods. The methods include receiving an image from a mammogram, removing noise from the image thereby creating a de-noised image, computing a point of interest on the de-noised image, creating a mesoscale region of interest on the de-noised image, computing a connectivity for the mesoscale region of interest, identifying a connected component using the computed connectivity, where the connected component represents a branch of a global curvilinear structure, selecting a set of branches based on a physical property for each branch of the global curvilinear structure, pruning each branch based on an error-tolerant, adaptive polynomial fit, identifying remaining regions of interest in each pruned branch, and growing a chain formed by remaining points of interest included in the remaining regions of interest, where the chain represents a macroscopic, global curvilinear calcified arterial structure.

In an aspect of the invention, quantitation of the calcified arterial structures may be used as a biomarker for risk stratification of heart disease.

These and other features, aspects and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein

FIG. 5 is a flow chart of a method for a third phase of a method for detecting local calcified microstructures and constructing global (calcified) arterial structures.

FIG. 6 is a flow chart of a method for a fourth phase of a method for detecting local calcified microstructures and constructing global (calcified) arterial structures.

FIGS. 7-29 illustrate representative images.

DETAILED DESCRIPTION

Figure 1:
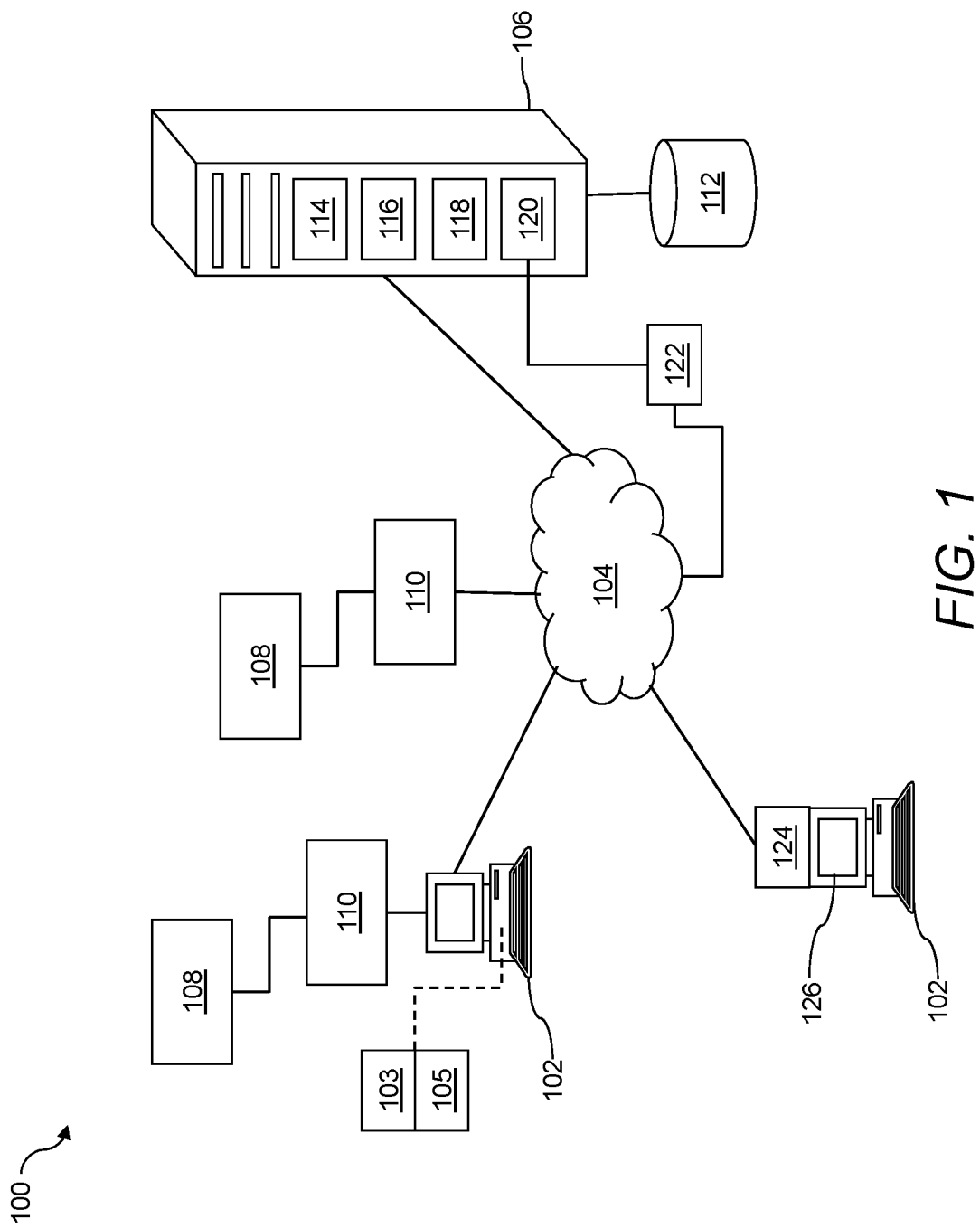
FIG. 1 illustrates a networked system for detecting calcified structures.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," "substantially," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms.

In general, described herein are devices, systems, and methods for detecting calcified structures, e.g., for constructing global (calcified) arterial structures.

Breast arterial calcifications ("BACs"), through their opacity to X-rays, generally form distinct, granular, microscopic structures on mammogram (MG) images. For MG images where low X-ray exposure is represented by bright pixel intensity (and conversely, where high X-ray exposure is represented by dark pixel intensity), BACs generally appear as bright microstructures with sharp spatial gradients. These bright microstructures may organize into macroscopic curvilinear structures that delineate the calcified portions of breast arteries, and typically contain bifurcation/branch points where the arteries bifurcate. A goal of the disclosed embodiments is to detect local calcified microstructures from which one can construct global (calcified) arterial structures. The resulting global structures may have various applications, in particular in detecting and quantitating the degree of arterial calcification in breast tissue which may indicate of arterial calcification in other tissues. As such measurement of BAC may be used as predictor of disease in such tissues.

By way of background, it is noted that calcified arteries may be prominent structures in mammograms which can lead to false identification of suspicious micro-calcification lesions in the mammograms. As such it may be important to remove as many of these global arterial structures as possible. This has led to the present global arterial mapping algorithm of the present invention, which is applicable in predicting arterial calcification in various tissues. As such, the present global arterial mapping algorithm provides a reliable and accurate method of evaluation of BAC.

Although devices, systems, and methods discussed herein generally describe the detection of arterial calcifications, detection and quantification of other cells, physiological anomalies, and the like, may also or instead be enabled by the devices, systems, and methods discussed herein. Although certain embodiments discussed herein are described for the specific use case of BAC, and methods discussed herein can be adapted for other tissue arterial calcifications. Furthermore, although embodiments generally described herein are directed to the use case of medical images of human tissue, the embodiments may also or instead be applicable to animal tissue, for example.

In general, the devices, systems, and methods discussed herein may utilize medical image analysis, which may be automated through the use of various hardware and software as described herein. The medical image analysis techniques discussed herein may thus be used for the detection of arterial calcifications and/or for the construction of global arterial structures.

FIG. 1 illustrates a networked system for detecting calcified structures. As shown in the figure, the system 100 may include a client server implementation of detecting calcified structures, e.g., for the construction of global arterial structures. The system 100 may include one or more computing devices 102 that are each used by a user or an administrator to couple to and interact with, over a network 104, a backend component 106. Although a client server/web implementation of the system 100 is shown, the system 100 may also be implemented using a software as a service (SaaS) model, a standalone computer, and other computer architectures.

The one or more computing devices 102 may include a processor based computing device that has at least one processor 103, a memory 105, persistent storage, a display, and communication circuits so that each computing device 102 can communicate with the backend component 106, display information related to calcified structures, submit pieces of medical information to the backend component 106, or otherwise interact with the backend component 106 or another component of the system 100. For example, the computing device 102 may include without limitation a smartphone device, a tablet computer, a personal computer, a laptop computer, a terminal device, a cellular phone, and the like. In some embodiments, the computing device 102 may execute an application, such as a known browser application or mobile application, that facilitates the interaction of the computing device 102 with the backend component 106. The one or more computing devices 102 may also or instead include other devices, for example including client devices such as a computer or computer system, a Personal Digital Assistant, a mobile phone, or any other mobile or fixed computing device.

The computing device 102 may include a desktop computer workstation. The computing device 102 may also or instead be any device suitable for interacting with other devices over a network 104, such as a laptop computer, a desktop computer, a personal digital assistant, a tablet, a mobile phone, a television, a set top box, a wearable computer, and the like. The computing device 102 may also or instead include a server or it may be disposed on a server, such as any of the servers described herein.

The computing device 102 may be used for any of the entities described herein. In certain aspects, the computing device 102 may be implemented using hardware (e.g., in a desktop computer), software (e.g., in a virtual machine or the like), or a combination of software and hardware. The computing device 102 may be a standalone device, a device integrated into another entity or device, a platform distributed across multiple entities, or a virtualized device executing in a virtualization environment.

In general, the computing device 102 may include a processor 103, a memory 105, a network interface 124, a data store, and one or more input/output interfaces. The computing device 102 may further include or be in communication with peripherals and other external input/output devices that might connect to the input/output interfaces.

The processor 103 may be any processor or other processing circuitry capable of processing instructions for execution within the computing device 102 or system 100. The processor 103 may include a single-threaded processor, a multi-threaded processor, a multi-core processor and so forth. The processor 103 may be capable of processing instructions stored in the memory 105 or the data store.

The memory 105 may store information within the computing device 102. The memory 105 may include any volatile or non-volatile memory or other computer-readable medium, including without limitation a Random Access Memory (RAM), a flash memory, a Read Only Memory (ROM), a Programmable Read-only Memory (PROM), an Erasable PROM (EPROM), registers, and so forth. The memory 105 may store program instructions, program data, executables, and other software and data useful for controlling operation of the computing device 102 and configuring the computing device 102 to perform functions for a user. The memory 105 may include a number of different stages and types of memory for different aspects of operation of the computing device 102. For example, a processor may include on-board memory and/or cache for faster access to certain data or instructions, and a separate, main memory or the like may be included to expand memory capacity as desired. All such memory types may be a part of the memory 105 as contemplated herein.

The memory 105 may, in general, include a non-volatile computer readable medium containing computer code that, when executed by the computing device 102 creates an execution environment for a computer program in question, e.g., code that constitutes processor firmware, a protocol stack, a database management system, an operating system, or a combination of the foregoing, and/or code that performs some or all of the steps set forth in the various flow charts and other algorithmic descriptions set forth herein. While a single memory 105 is depicted, it will be understood that any number of memories may be usefully incorporated into the computing device 102. For example, a first memory may provide non-volatile storage such as a disk drive for permanent or long-term storage of files and code even when the computing device 102 is powered down. A second memory such as a random access memory may provide volatile (but higher speed) memory for storing instructions and data for executing processes. A third memory may be used to improve performance by providing higher speed memory physically adjacent to the processor 103 for registers, caching, and so forth. The processor 103 and the memory 105 can be supplemented by, or incorporated in, logic circuitry.

The network 104 may include a communications path such as a wired or wireless network that uses a communications protocol and a data protocol, such as HTTP or HTTPS and HTML or JSON or REST, to allow each computing device 102 to interact with the backend component 106. The network 104 may be a wired network, a wireless computer network, a wireless digital data network, a cellular wireless digital data network, or a combination of these networks that form a pathway between each computing device 102 and the backend component 106.

The network 104 may also or instead include any data network(s) or internetwork(s) suitable for communicating data and control information among participants in the system 100. This may include public networks such as the Internet, private networks, and telecommunications networks such as the Public Switched Telephone Network or cellular networks using third generation cellular technology (e.g., 3G or IMT-2000), fourth generation cellular technology (e.g., 4G, LTE. MT-Advanced, E-UTRA, etc.) or WiMax-Advanced (IEEE 802.16m)) and/or other technologies, as well as any of a variety of corporate area, metropolitan area, campus or other local area networks or enterprise networks, along with any switches, routers, hubs, gateways, and the like that might be used to carry data among participants in the system 100. The network 104 may also include a combination of data networks, and need not be limited to a strictly public or private network. The participants in the system 100 may each be configured with a network interface 124 for communications over the network.

A user 108 of the system 100 may be a patient, a doctor, a radiologist, a health care organization, an image analyst, and the like. The user 108 may, using the computing device 102, submit one or more pieces of medical information 108 for quantification by the system 100 and/or receive, from the backend component 106, information based on the received pieces of medical information 110. The backend component 106 may include storage 112 coupled to the backend component 106 (e.g., a memory, a database, and the like) that may store various data associated with the system 100 including a plurality of pieces of medical information 110 that may be used to generate information based on the detected calcifications as described herein, user data associated with the system, and the like. The storage 112 may be implemented using a known software based or hardware based storage system.

The backend component 106 may be implemented using one or more computing resources including without limitation a processor 114, a memory 116, persistent memory/storage, and the like. By way of example, each computing resource may be a blade server, a server computer, an application server, a database server, a cloud computing resource and the like. When the system 100 is implemented as the client server architecture as shown in the figure, the backend component 106 may have a web server 118 or the like that manages the connections and interactions with each computing device 102, generates HTML code to send to each computing device 102, receives data from each computing device 102, and the like. The web server 118 may be implemented in hardware or software.

The backend component 106 may include an image analysis engine 120 that analyze pieces of medical information 110 about tissue. The image analysis engine 120 may generate any indications of calcifications in any regions of the tissue and may generate a global structure 122. The image analysis engine 120 may receive/obtain the pieces of medical information 110 about tissue from a computing device 102, over a computer network from a third-party, or from the storage 112 of the system 100. The global structure 122 may be transmitted through the network 104, e.g., for display on the one or more computing devices 102. The image analysis engine 120 may be implemented in software or hardware. When the image analysis engine 120 is implemented in software, the image analysis engine 120 (and its components) may comprise a plurality of lines of computer code that may be stored in a memory 116 and executed by a processor 114 of the backend component 106 so that the processor 114 is configured to perform the processes of the image analysis engine 120 (and its components) as described herein. When the image analysis engine 120 is implemented in hardware, the image analysis engine 120 (and its components) may comprise a microcontroller, a programmable logic device, an application specific integrated circuit, or other hardware device in which the hardware device performs the processes of the image analysis engine 120 (and its components) as described herein. The image analysis engine 120 may include an algorithm or series of algorithms that assist in generating the global structure 122 as discussed herein.

The one or more pieces of medical information 108 may include a medical image. The medical image may include an x-ray image, e.g., a mammogram and the like. The medical image may also or instead include magnetic resonance (MRI) images, computerized tomography (CT) scan images, ultrasound images, and so on.

The system 100 may instead be implemented as part of a standalone computer implementation. In this implementation, the image analysis engine 120 may be executed on one of the computing devices 102, e.g., by the processor 103 and memory 105, based on one or more pieces of medical information 110 stored in the computing device 102 or input into the computing device 102. The computing device 102 may have a display 126 and any other additional hardware including without limitation input/output devices such as a keyboard and a mouse. The display 126 may include a user interface, e.g., a graphical user interface. The computing device 102 may also include the processor, and a persistent storage device such as flash memory or a hard disk drive and memory, such as DRAM or SRAM, that are connected to each other. When the computing device 102 is used to implement the system and the image analysis engine 120 is implemented in software, the memory 105 may store the image analysis engine 120 and an operating system and the processor 103 of the system may execute a plurality of lines of computer code that implement the image analysis engine 120 so that the processor 103 of the computer system is configured to perform the processes of the image analysis engine 120 as described herein.

The image analysis engine 120 may, in general, receive one or more pieces of medical information 110 about a piece of tissue of a patient and, for each piece of tissue for the patient, generate information related thereto. The piece of tissue may include without limitation any piece of human tissue or any piece of animal tissue that may have calcifications.

Figure 2:
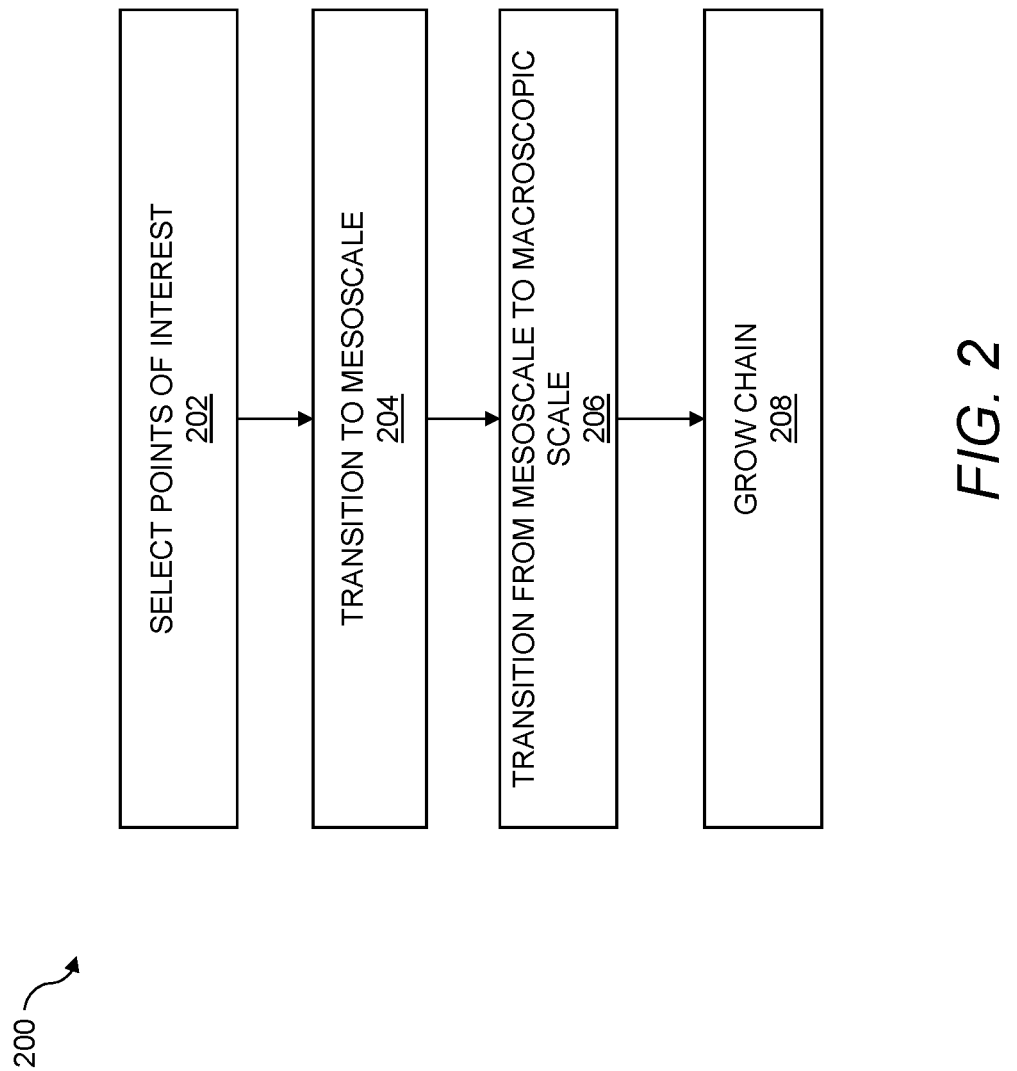
FIG. 2 is a flow chart of a method for detecting local calcified microstructures and constructing global (calcified) arterial structures.

FIG. 2 is a flow chart of a method for detecting local calcified microstructures and constructing global (calcified) arterial structures. The method 200 may in general represent main phases for an algorithm to perform technique for detecting calcified microstructures and constructing global arterial structures.

As shown by step 202, the method 200 may include selecting points of interest (POIs).

As shown by step 204, the method 200 may include transitioning to mesoscale.

As shown by step 206, the method 200 may include transitioning from mesoscale to macroscopic scale.

As shown by step 208, the method 200 may include growing the chain.

Thus, in an aspect, the algorithm includes four distinct phases. In the first phase, POIs may be located. In the second phase, POIs may be grouped and mapped onto mesoscale regions of interests (ROIs), e.g., in order to increase computational performance. In the third phase, ROIs may be grouped into branches of the global curvilinear structures, and spurious ROIs that do not belong such structures (e.g., false-positive ROIs) are eliminated through an error-tolerant, adaptive polynomial fit, and the selected ROIs are replaced by their constituent POIs to provide better algorithmic efficacy. In the fourth phase, these selected POIs may be used as "growth sites" to which micro-calcifications, provided by a Q-algorithm (e.g., as described in International Publication PCT/US2016/054074, and is hereby incorporated by reference herein in its entirety), attach themselves. The calcified arterial structures may grow until saturation occurs, i.e., the number of micro-calcifications contained in the structures becomes unchanged with further attempts at growth. This process may represent a direct analogy to the physical process of polymer growth in which polymer growth sites serve as seed points for the polymer chains to grow. Once the polymer chains begin to form, they may only growth lengthwise, i.e., growth can only occur at the endpoints of the polymer chain. In summary, given a set of micro-calcifications from the Q-algorithm, the global arterial mapping algorithm may yield global curvilinear structures. Those micro-calcifications that are not part of these global curvilinear structures may thus be identified. One may then retain the global arterial structures and discard the remainder.

FIGS. 3-6 are flow charts representing the steps taken in various phases of the method for detecting local calcified microstructures and constructing global (calcified) arterial structures as described in an embodiment herein. FIGS. 7-45 illustrate representative images, which are included to further illustrate the various steps discussed in the methods of FIGS. 3-6.

Figure 3:
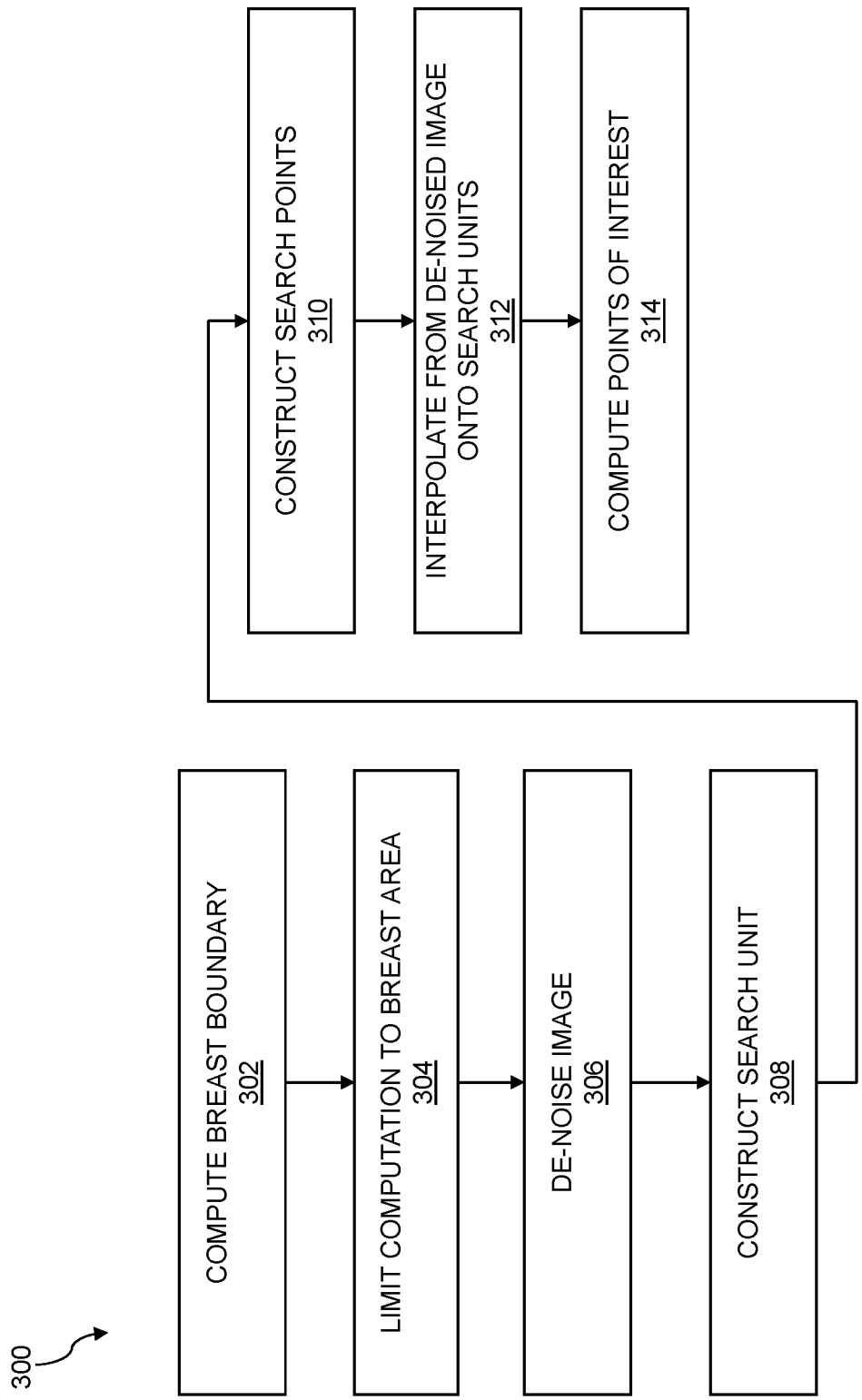
FIG. 3 is a flow chart of a method for a first phase of a method for detecting local calcified microstructures and constructing global (calcified) arterial structures.

FIG. 3 is a flow chart of a method for a first phase of a method for detecting local calcified microstructures and constructing global (calcified) arterial structures. In other words, the figure represents steps that may be taken by in an algorithmic technique related to selecting points of interest (POIs).

Figure 9:
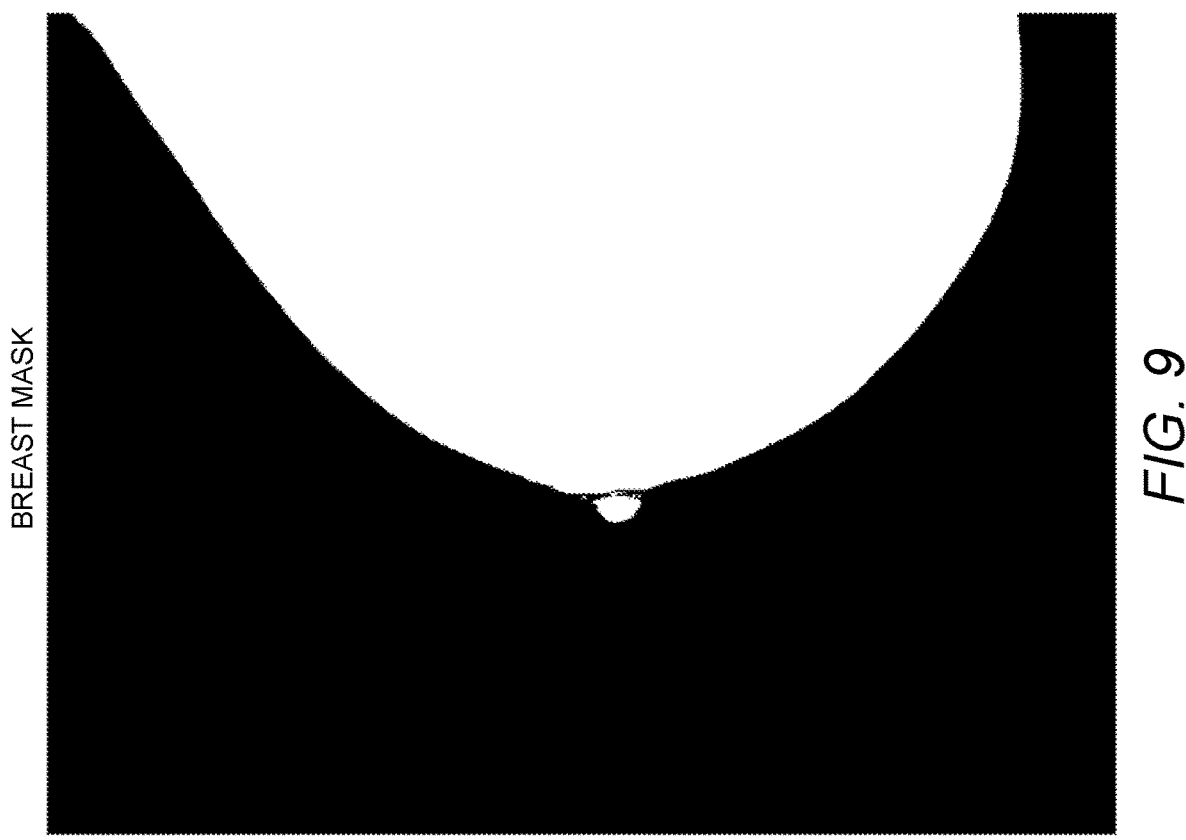

As shown in step 302, the method 300 may include computing the breast boundary. Given an image with pixel intensity I(x,y) (see FIG. 7), the breast boundary may be computed (shown as the curve 802 in FIG. 8), represented as a parametric curve $(B_x(xi), B_y(xi))$, where xi is the parametric quantity, and the breast mask—a Boolean array where a logical "true" indicates a point interior to the breast, and conversely, a logical "false" indicates a point outside of the breast, as shown in FIG. 9.

As discussed above, implementations may be used on other tissue in addition to or instead of the breast, and thus the steps may be adjusted accordingly to accommodate the boundary/areas of the other tissue regions.

Figure 11:
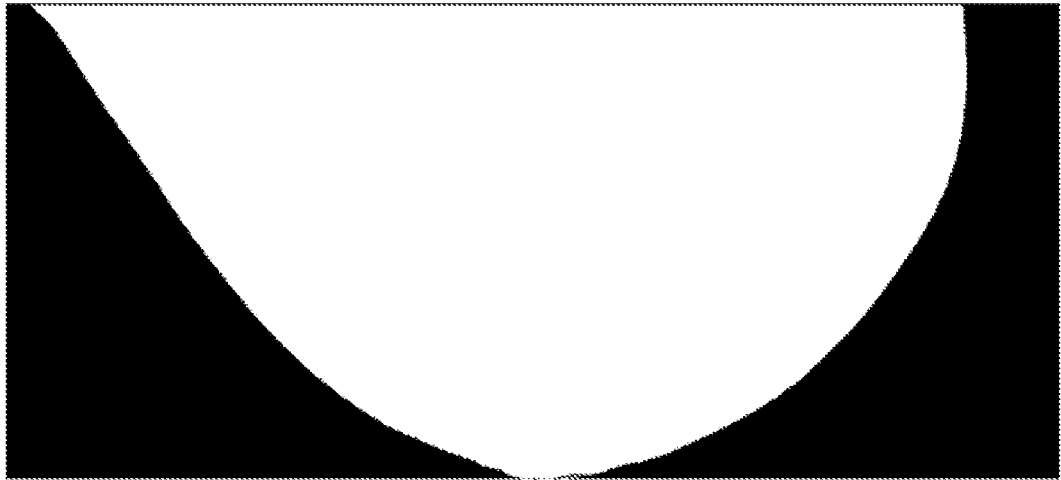
Figure 10:
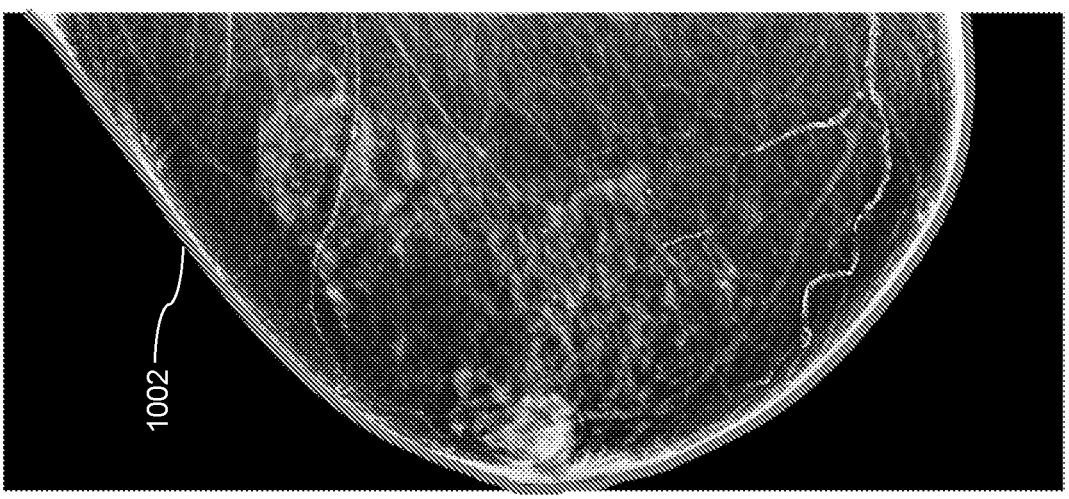
Figure 13:
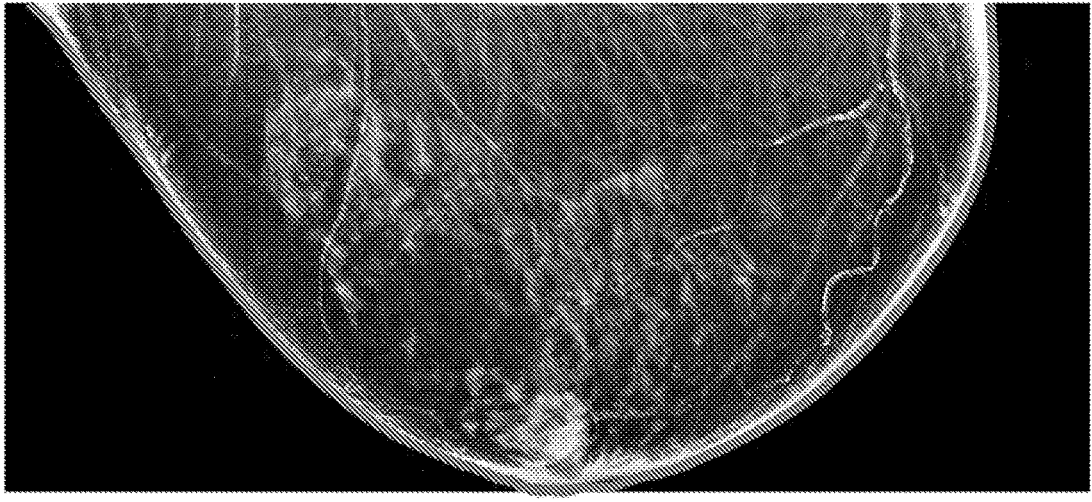
Figure 12:
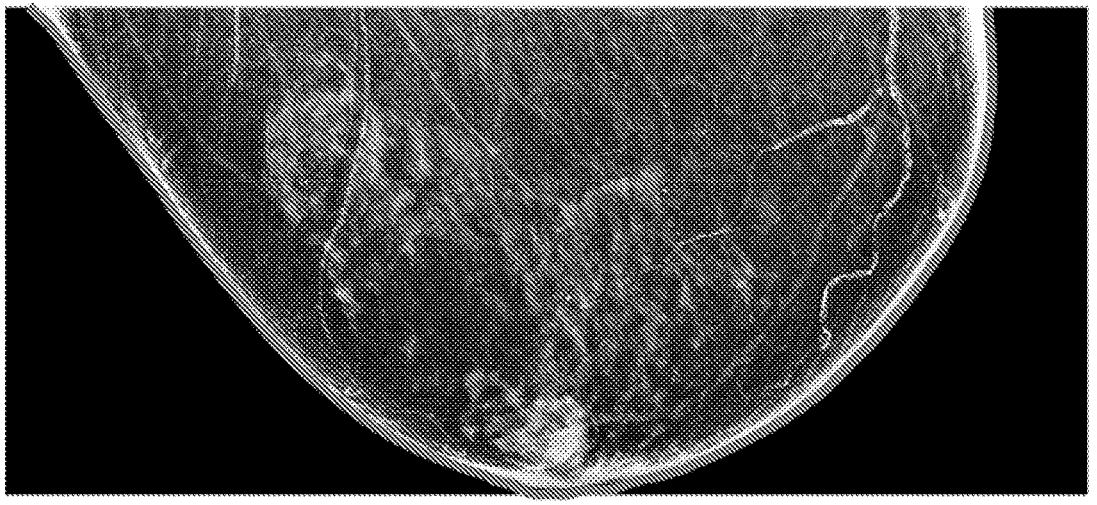

As shown in step 304, the method 300 may include limiting computation to the breast area. For computation performance without loss of accuracy, the region beyond the apex of the breast contour may be excluded from computations. FIGS. 10 and 11 indicate regions where actual computations are applied in an example. Specifically, in FIG. 10, the sub-region of the original image where computations may be applied is shown. The region beyond the apex of the breast contour (beyond the curve 1002) has been excluded. The global maximum of the pixel intensity, $I_0 = \max(I(x,y))$, may be computed for subsequent use. In FIG. 11, the breast mask corresponding to the sub-region from FIG. 10 is shown.

As shown in step 306, the method 300 may include de-nosing the original image. Prior to any further processing, the image I(x,y) shown in FIG. 10 may be pre-processed with a wavelet filter (Coiflet 1) to remove short scale-length noise, resulting in a de-noised image $I_{DN}(x,y)$. Hence forth, the de-noised image $I_{DN}(x,y)$ may be used exclusively for all processing. Examples of the "before" (FIG. 12) and "after" (FIG. 13) images are provided. Specifically, the original image I(x,y) (FIG. 12) may be de-noised with a wavelet filter to remove short scale-length noise, yielding the de-noised image $I_{DN}(x,y)$ (FIG. 13) to be used for all further processing.

As shown in step 308, the method 300 may include constructing a basic search unit. The basic search-unit may be a circle with radius of r (centered at the origin), where r is varied to optimize the algorithm's performance. In an example, r=3.5 millimeter:

$$x_0(\text{theta}) = r^* \cos(\text{theta})$$

$$y_0(\text{theta}) = r^* \sin(\text{theta})$$

where theta varies between 0 to 360 degrees in 4 degree increments. Given a "search point," the search-unit associated with this search-point may be formed by simple shifting of the basic-search unit in the 2D coordinate plane:

$$x_S = x_{SP} + x_0(\text{theta})$$

$$y_S = y_{SP} + y_0(\text{theta})$$

It is noted that by defining a basic search-unit, one may obtain the (x,y) coordinates of any search unit circle by a simple linear translation—a much more computationally efficient operation compared to re-computing the trigonometric functions and multiplying these trigonometric functions by the radius repeatedly.

As shown in step 310, the method 300 may include constructing search points. In an aspect, all local maxima within the breast mask are chosen as search-points, shown as the dots 1402 in FIG. 14. In other words, as shown in FIG. 14, each local maximum within the breast region may be selected as a search-point, denoted by the dots 1402.

Figure 16:
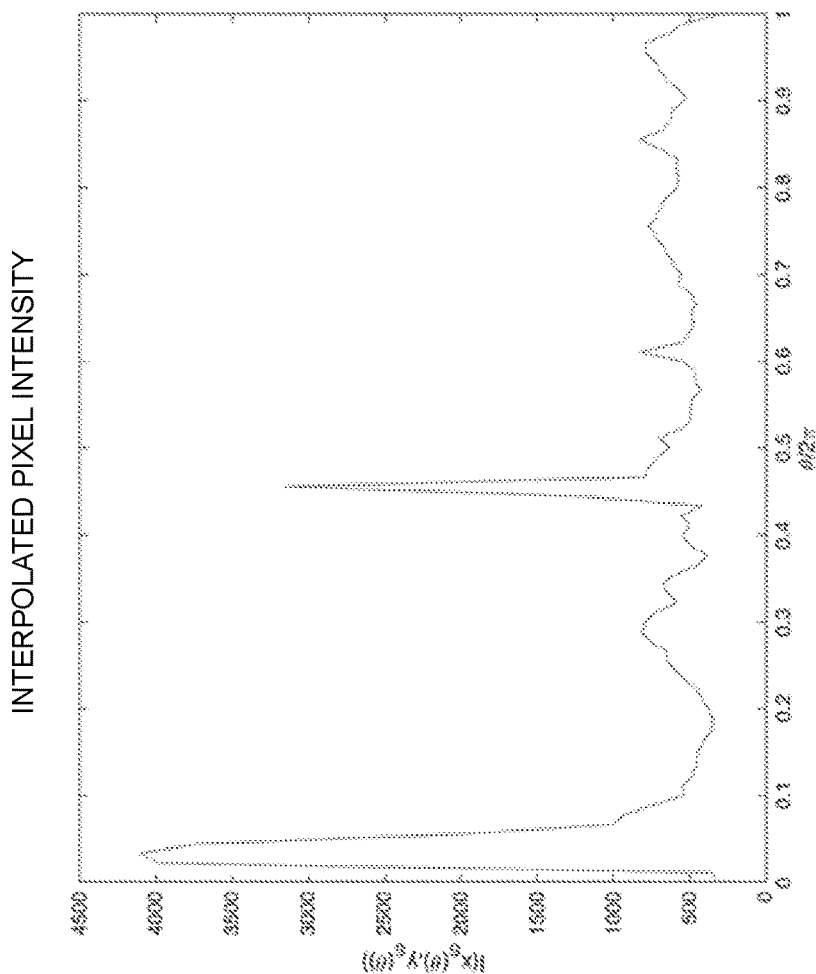
Figure 15:
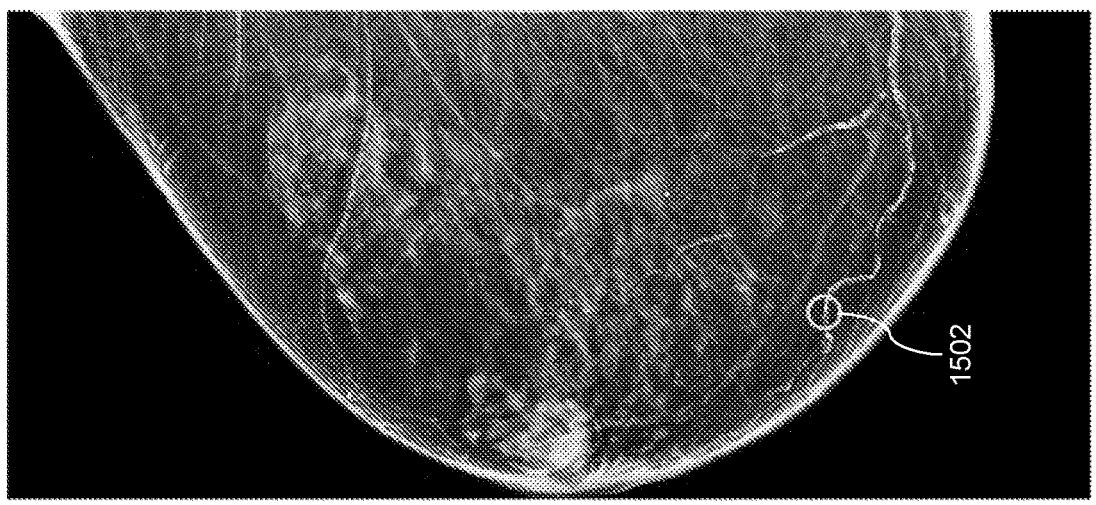
Figure 18:
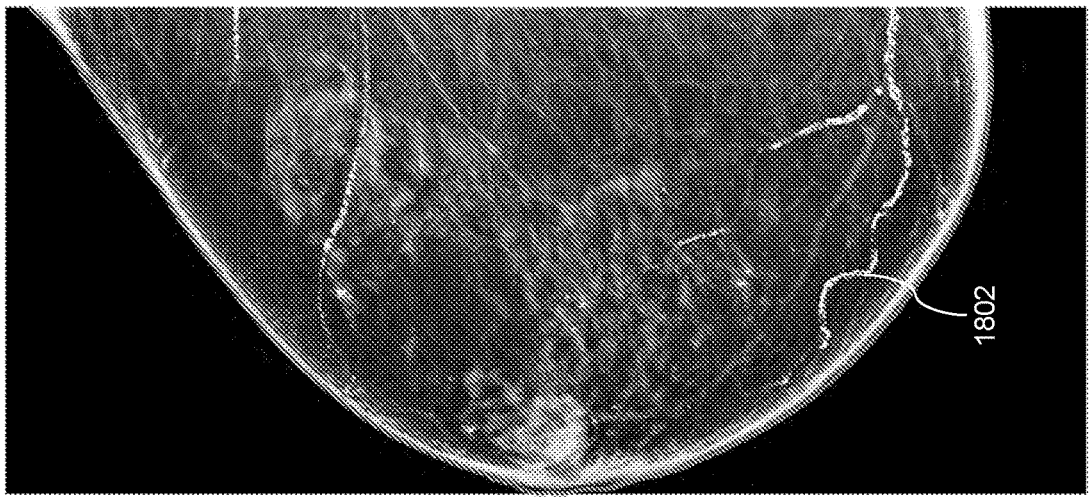
Figure 17:
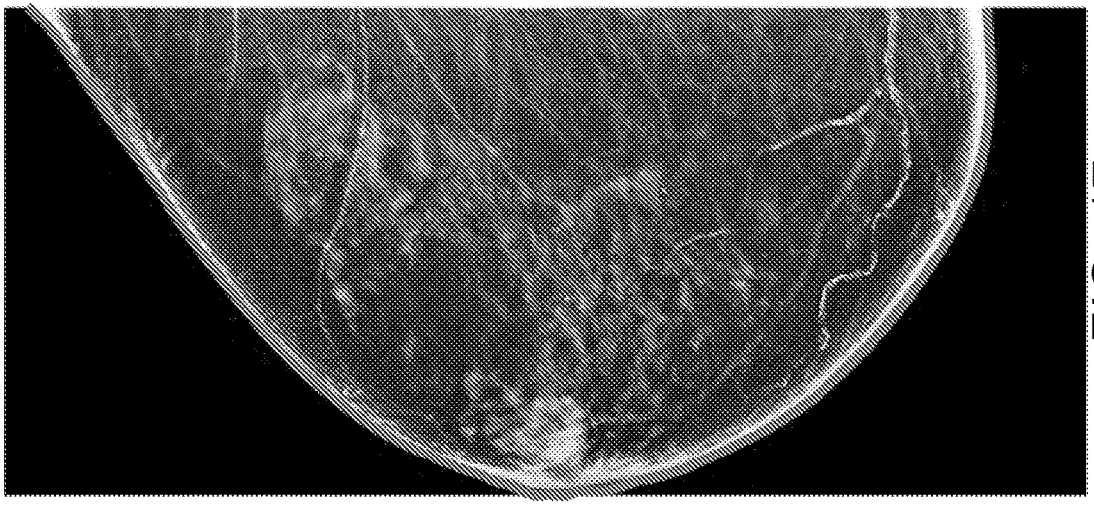

As shown in step 312, the method 300 may include interpolating from the de-noised image onto the search units. For each search-unit associated with a search point, the pixel intensity may be interpolated from onto the search-unit circle by bilinear interpolation. For the purpose of illustration, one representative search unit circle 1502, superimposed onto the image, is shown in FIG. 15, and the corresponding interpolated pixel intensity is shown in FIG. 16. As shown in FIG. 16, the pixel intensity may be interpolated from the de-noised image $I_{DN}(x,y)$ onto the search-unit circle depicted in FIG. 15 by bilinear interpolation.

As shown in step 314, the method 300 may include computing points of interest (POIs). A POI may be defined as any point on a search-unit circle that satisfies both conditions enumerated below:

$$\frac{\langle I_{DN}(x_s(\theta), y_s(\theta))\rangle}{\max(I_{DN}(x_s(\theta), y_s(\theta)))} < \tau_1,$$

$$\frac{\langle I_{DN}(x_s(\theta), y_s(\theta))\rangle}{I_0} > \tau_2,$$

And, in an aspect, the point $(x_S(\text{theta}), y_S(\text{theta}))$ must be at least 5 millimeter away from the breast boundary, i.e., $$\min(d((\theta),\xi)) \geq 5 \text{ millimeter}$$

$$d=[(x_s(\theta)-B_x(\xi))^2+(y_s(\theta)-B_y(\xi))^2]^{1/2}$$

Other distances may also or instead be used.

The set of thresholds $(\tau_1, \tau_2)$ may be chosen to optimize the algorithm's performance. In an illustrative example, $(\tau_1, \tau_2)=(0.5, 0.1)$. For the image shown in FIG. 17, the POIs, selected as described above, are depicted by the dots 1802 in FIG. 18. Thus, the dots 1802 denote the selected POIs in an illustrative example.

Figure 4:
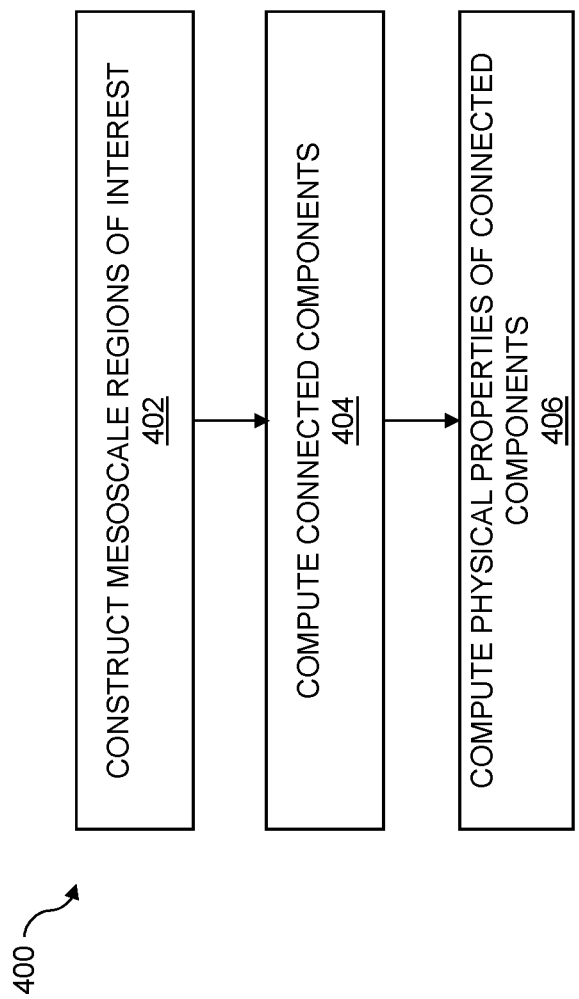
FIG. 4 is a flow chart of a method for a second phase of a method for detecting local calcified microstructures and constructing global (calcified) arterial structures.
Figure 8:
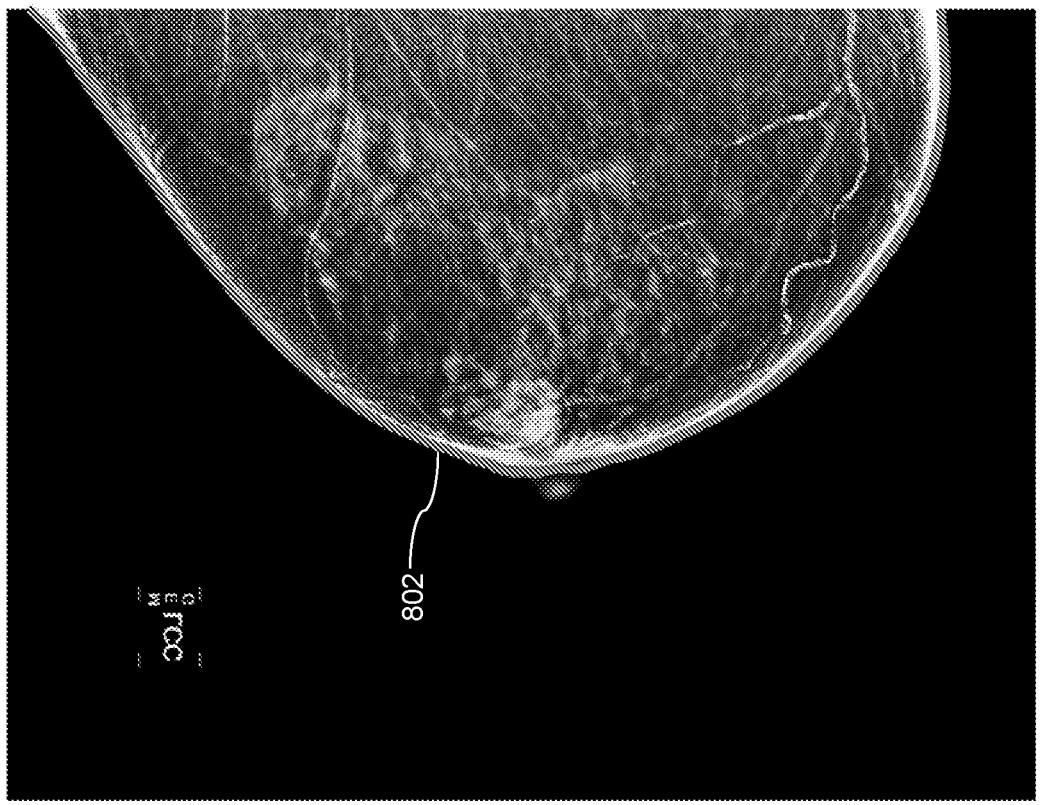
Figure 7:
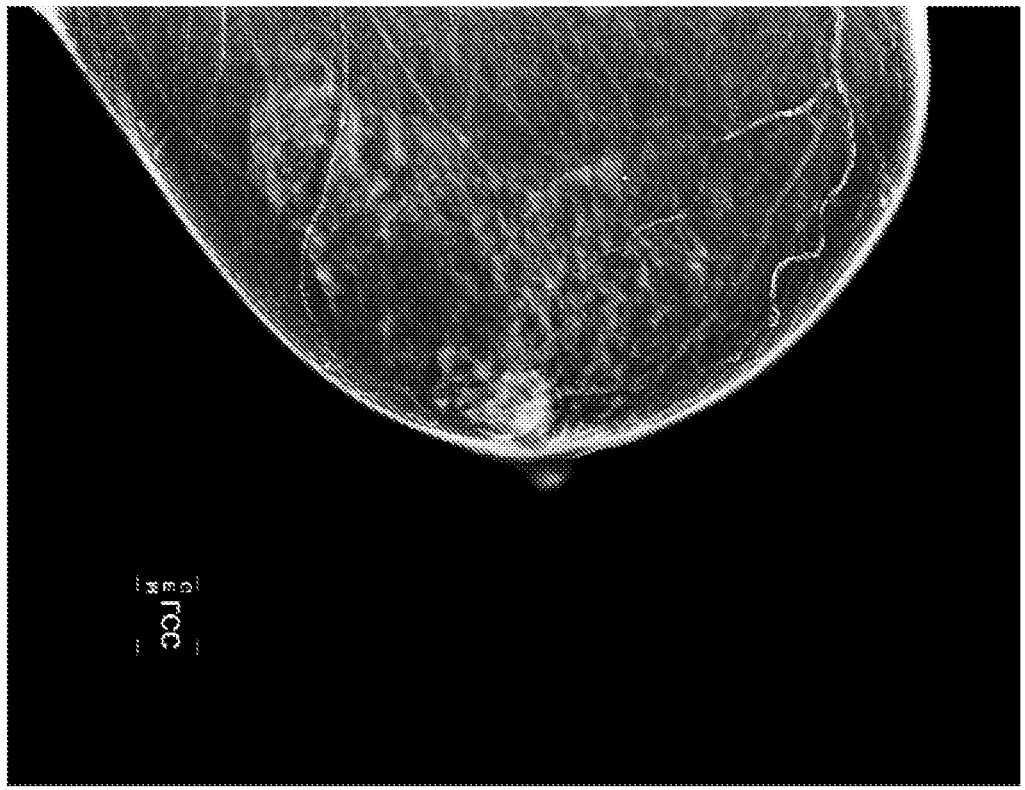

FIG. 4 is a flow chart of a method for a second phase of a method for detecting local calcified microstructures and constructing global (calcified) arterial structures. In other words, the figure represents steps that may be taken by in an algorithmic technique related to transitioning to mesoscale.

As shown in step 402, the method 400 may include constructing mesoscale regions of interest (ROIs). The mesoscale ROIs may be constructed, beginning from the upper-left corner of the image, in a 2D regular grid with spacing D in both the horizontal and vertical directions. The physical size of D may be chosen to optimize the performance of the algorithm. In an illustrative example, D=1.3 millimeters.

Figure 19:
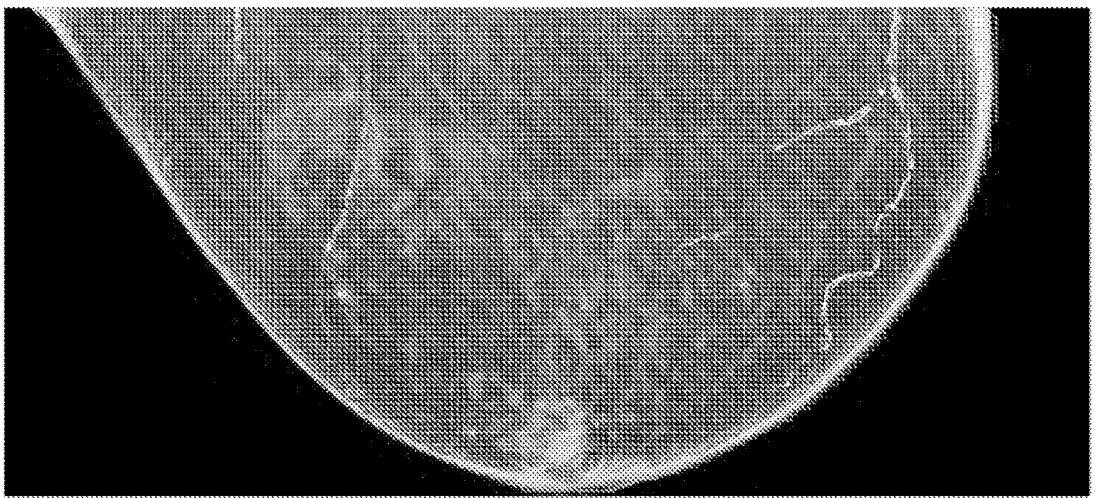

FIG. 19 shows the mesoscale ROIs superimposed on the image $I_{DN}(x,y)$, and the POIs computed above (FIG. 18) are shown in the background. Only ROIs that overlap with the breast mask may be shown, and these ROIs may be the only ones that enter subsequent computations.

Figure 21:
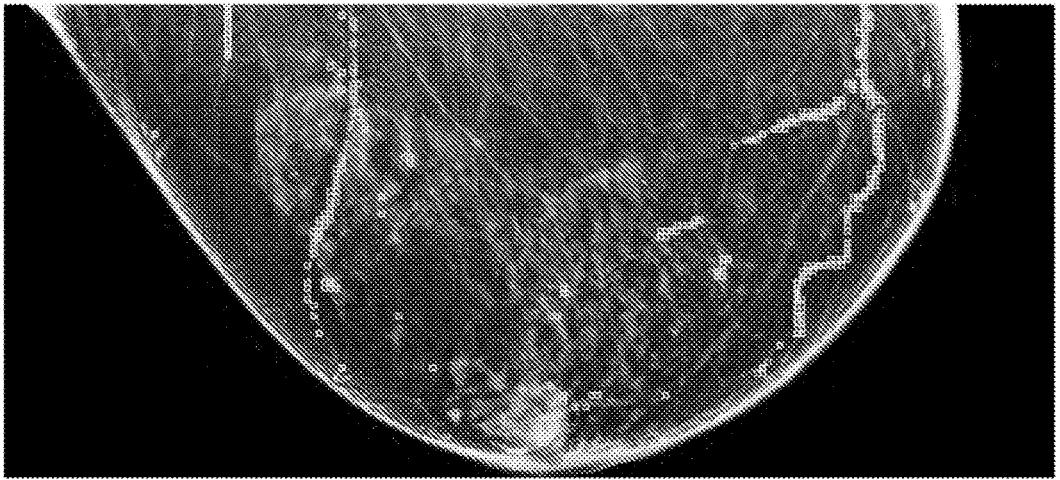
Figure 20:
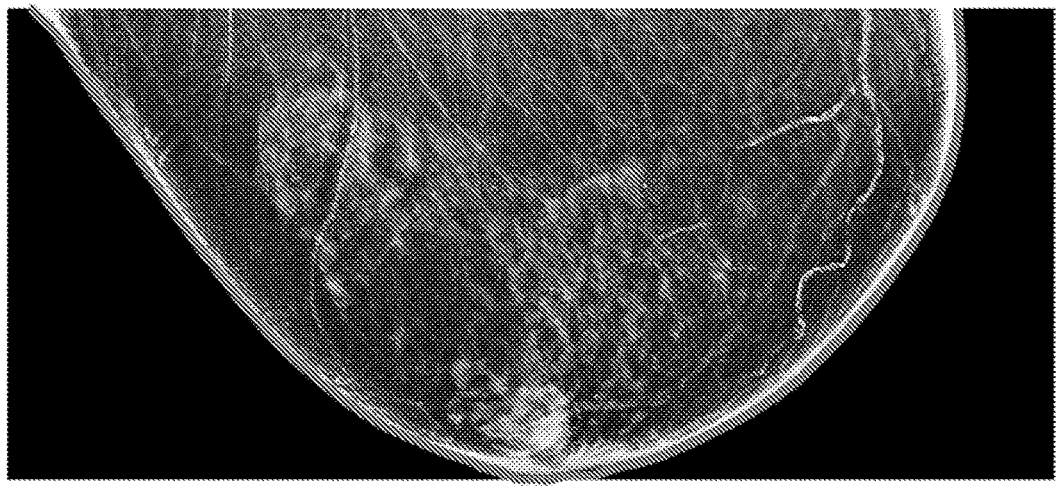

As shown in step 404, the method 400 may include computing the connected components of the ROIs. For each ROI, the number of POIs it contains may be computed, and its connectivity index (i.e., number of non-empty nearest-neighbors for the ROI) and which nearest neighbors are connected to it may be recorded. At most, each ROI may have 8 non-empty nearest neighbors (i.e., N, S, E, W, NE, NW, SE, SW). Isolated ROIs will have no nearest neighbor. Having computed each ROI's connectivity, one can determine the set of connected components, where each connected component is a set of ROIs in which each ROI has at least one nearest neighbor in the set and no nearest neighbor from a different set. The connected components corresponding to FIG. 20 are shown in FIG. 21 by way of example. Physically, each connected component may represent a "branch" of the global curvilinear structure. Thus, in FIG. 21, the connected components, or branches, corresponding to FIG. 20 are shown.

As shown in step 406, the method 400 may include computing physical properties of the connected components.

Each connected component may be associated with two numerical scores:

the connectivity ratio $C_i$ and the roundness ratio $R_i$, computed as follows:

$$C_i \equiv \frac{\sum_{j \in i} c_j}{N_i}$$

$$R_i \equiv \frac{P_i}{2(\pi A_i)^{1/2}}$$

where $j=1, 2, \ldots, N_i$ represents the set of ROIs belonging to the branch i. $P_i$ and $R_i$ are the perimeter and area of branch i, respectively.

FIG. 5 is a flow chart of a method for a third phase of a method for detecting local calcified microstructures and constructing global (calcified) arterial structures. In other words, the figure represents steps that may be taken by in an algorithmic technique related to transitioning from mesoscale to macroscopic scale.

Figure 23:
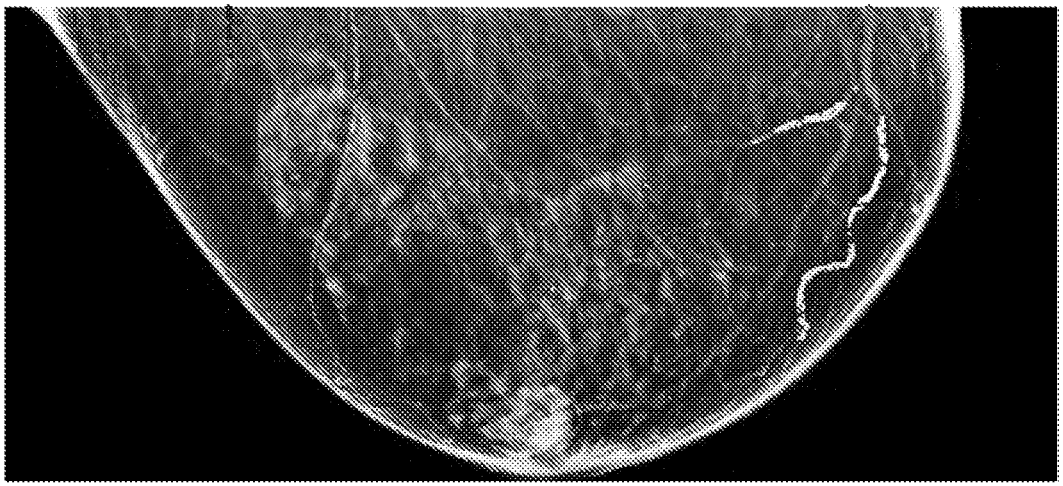
Figure 22:
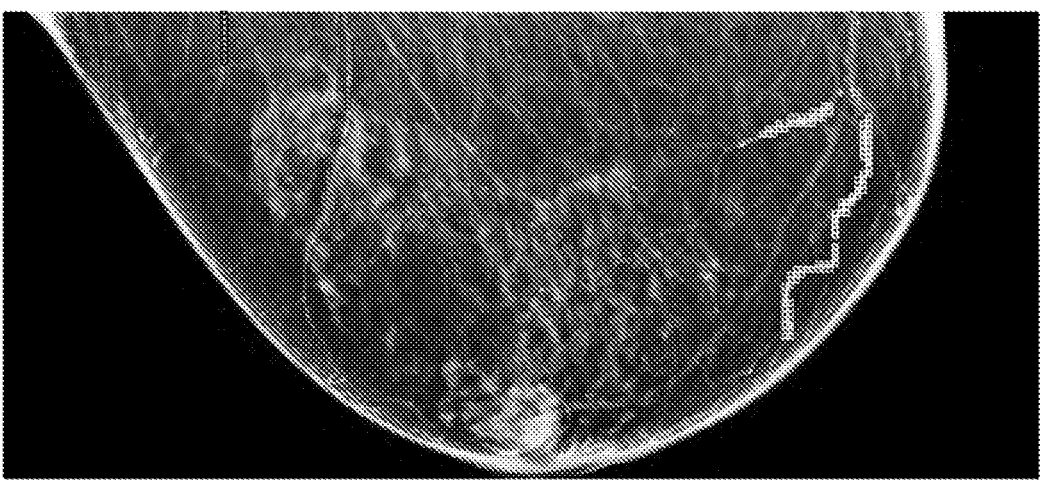

As shown in step 502, the method 500 may include down-selecting the branches. Branches may be selected in two stages. By way of example, in the first stage, a branch with index i may be discarded if any one of the following conditions is satisfied:

$N_i \leq 4$
$N_i=5$ and $C_i>12$
$N_i=6$ and $C_i>14$
$N_i=7$ and $C_i>20$
$N_i=8$ and $C_i>26$ By way of example, in the second stage, a branch with index i may retained if and only both conditions $C_i \leq C_{thres}$ and $R_i \geq R_{thres}$ are satisfied. The thresholds $C_{thres}$ and $R_{thres}$ may be selected to optimize the algorithm's performance. In an illustrative example, $C_{thres}=5.69$ and $R_{thres}=1.49$. Physically, these conditions may be selected to favor long curvilinear structures, which inherently have larger roundness ratio $R_i$ and smaller connectivity ratio $C_i$ than roundish structures. After the two stages of down-selection, the connected components that remain are shown in FIGS. 22 and 23. Each color/shade may denote a different connected component. It is noted that each branch may include multiple ROIs (square boxes), and each ROI may include multiple POIs. The POIs associated with the branches in FIG. 22 are shown in the same color codes/shades in FIG. 23.

As shown in step 504, the method 500 may include computing the physical properties of the ROIs. Each ROI with index i may be described by its mean-brightness $\beta_i$ and centroid location $(X_i, Y_i)$:

$$\beta_i = \frac{1}{M_i} \sum_{j \in i} I_{DN}(x_j, y_j)$$

$$X_i = \frac{1}{M_i \beta_i} \sum_{j \in i} x_i I_{DN}(x_j, y_j)$$

$$Y_i = \frac{1}{M_i \beta_i} \sum_{j \in i} y I_{DN}(x_j, y_j)$$

Figure 24:
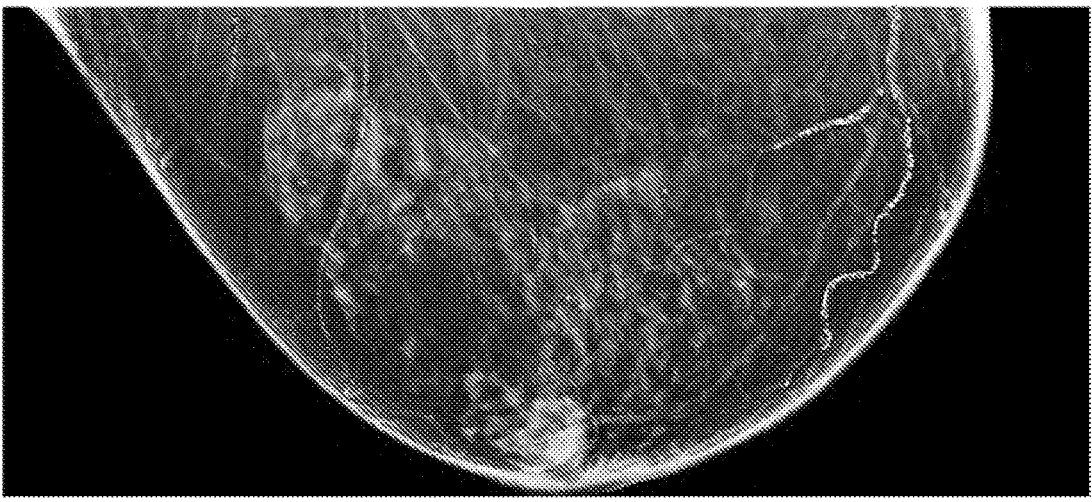

Each selected ROI may now be replaced with its centroid location computed above. FIG. 24 shows how each ROI in the branch may be replaced by a single point, its centroid location.

As shown in step 506, the method 500 may include pruning branches based on an error-tolerant, adaptive polynomial fit.

Figure 27:
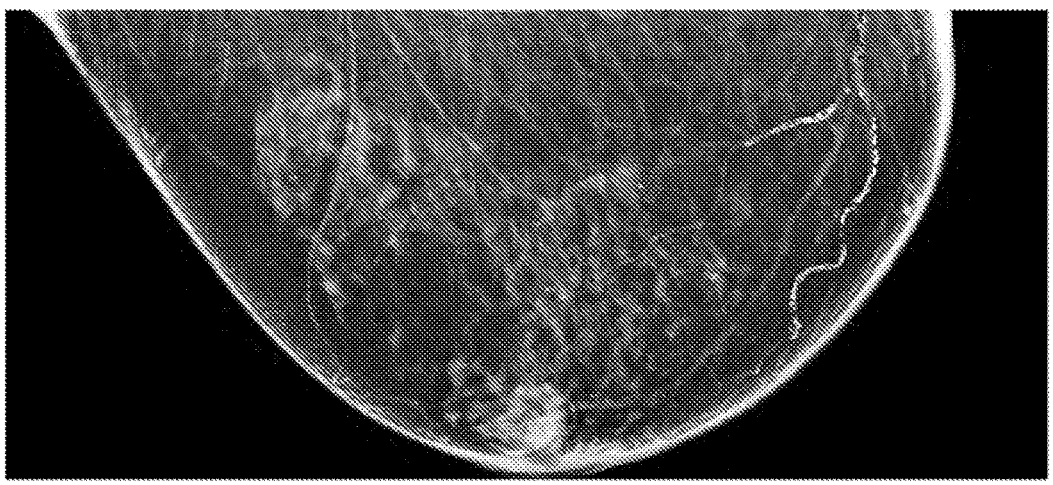
Figure 26:
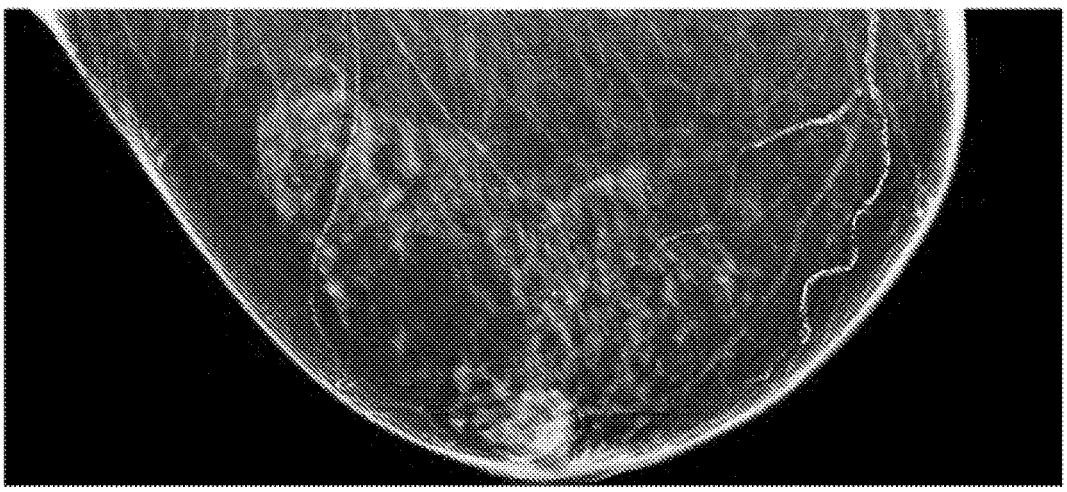
Figure 25:
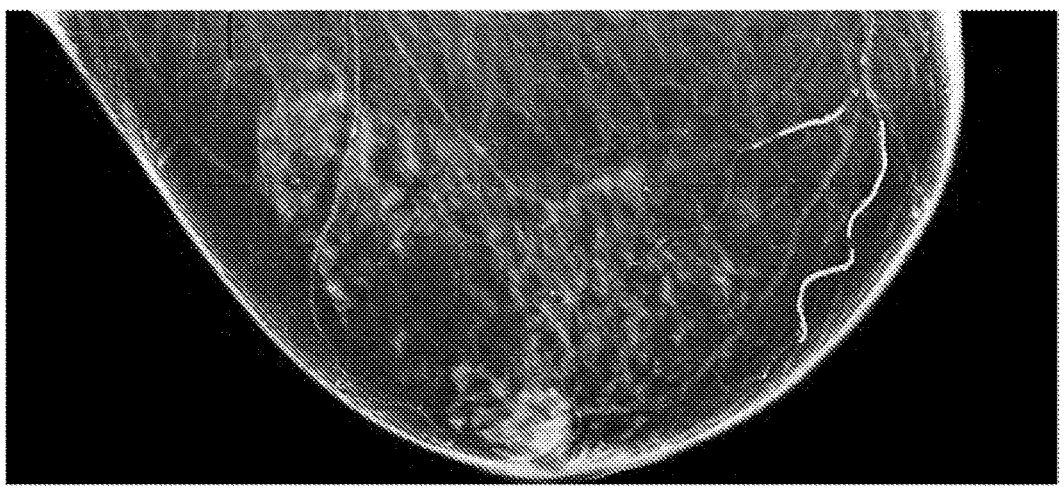

An error-tolerant, adaptive polynomial fit may be applied to each individual branch. Points (centroids) that are rejected by the polynomial fit may be discarded from the branch, and the corresponding ROI and POIs are also discarded. For the branches shown in FIG. 24, the corresponding polynomial fits are shown in FIG. 25, using the same color codes/shading. Likewise, the retained ROIs and their associated POIs are shown in FIGS. 26 and 27, respectively. Thus, FIG. 25 shows the error-tolerant, adaptive polynomial fits of the branches shown in FIG. 24; FIG. 26 shows the ROIs retained by the error-tolerant, adaptive polynomial fits shown in FIG. 25; and FIG. 27 shows the POIs associated with the ROIs in FIG. 26.

The POIs shown in FIG. 27 may form the curvilinear structure of the calcified arterials. These POIs may thus serve as "growth sites" to which the micro-calcifications attach themselves. The global calcified arterial structures may grow until saturation occurs, i.e., the number of micro-calcifications contained in the structure becomes unchanged with further attempts at growth. This process may be a direct analogy to the physical process of polymer growth in which polymer growth sites serve as seed points for the polymer chains to grow. Once the polymer chains begin to form, they can only growth lengthwise, i.e., growth can only occur at the endpoints of the polymer chain.

FIG. 6 is a flow chart of a method for a fourth phase of a method for detecting local calcified microstructures and constructing global (calcified) arterial structures. In other words, the figure represents steps that may be taken by in an algorithmic technique related to growing the chain (or using the analogy above, growing the polymer).

As shown in step 602, the method 600 may include detecting and selecting micro-calcifications. A Q-algorithm (e.g., as described in U.S. Prov. App. No. 62/236,168 filed on Oct. 2, 2015, which is appended hereto as Appendix A and is hereby incorporated by reference herein in its entirety) may detect and select micro-calcifications based on morphology, topology, and hierarchy of individual microstructures, and on their inter-structure relationship. In an example, the micro-calcifications detected and selected by a Q-algorithm are show in FIG. 28. In the figure, each micro-calcification is shown as a dot, representing its centroid location.

Figure 29:
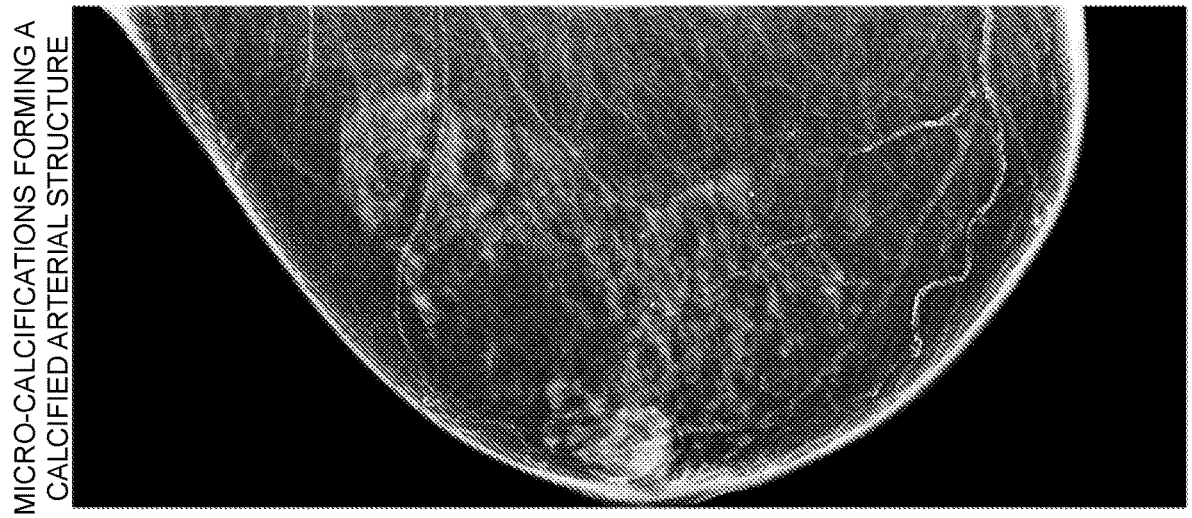

As shown in step 604, the method 600 may include growing the chain (or using the analogy above, growing the polymer). As discussed previously, the selected POIs, shown in FIG. 27 may serve as "polymer growth sites." Any micro-calcification site (shown in FIG. 28) within a polymer growth step lambda may become new polymer growth sites to which other micro-calcifications can be attached. The application of this "polymer growth" may be applied repeatedly until saturation is achieved, i.e., when the number of polymer growth sites becomes unchanged with further attempts to grow the polymer chain. In an illustrative example, lambda=2.5 millimeter. At saturation, the micro-calcifications attached the calcified arterial structure are shown in FIG. 29. In the figure, the dots represent centroid locations of micro-calcifications that form the calcified arterial structure.

The selected micro-calcifications shown in FIG. 29 may be the final product of a global arterial mapping algorithm. The micro-calcifications may form curvilinear branches, which themselves are constituents of a macroscopic, global curvilinear calcified arterial structure.

Figure 30:
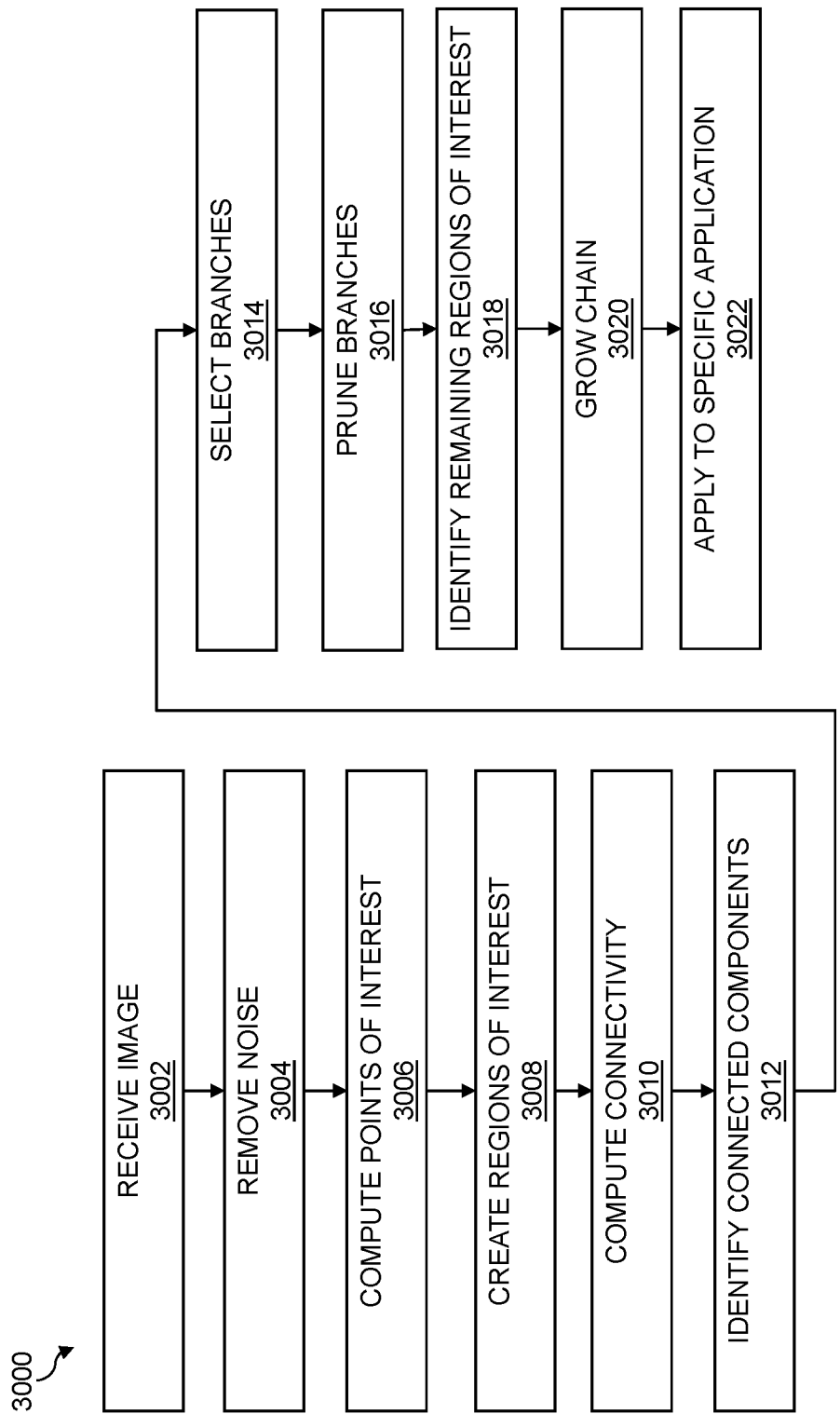
FIG. 30 is a flow chart of a method for detecting calcified microstructures and constructing global arterial structures.

FIG. 30 is a flow chart of a method for detecting calcified microstructures and constructing global arterial structures.

As shown in step 3002, the method 3000 may include receiving a first image of a breast of a patient obtained during a mammogram. Before or after removing noise from the first image, the image may be processed. This processing may include computing a boundary of the breast in the first image, and limiting computation to a breast area included within the boundary of the breast. Computing the boundary may include analysis of pixel intensity in the first image, and creating a first breast mask. The processing may also or instead include excluding a region beyond an apex of the boundary of the breast. The processing may also or instead include creating a second breast mask. The processing may also or instead include calculating a global maximum of pixel intensity.

As shown in step 3004, the method 3000 may include removing noise from the first image thereby creating a de-noised image. Removing noise may include applying a wavelet filter to remove short scale-length noise.

As shown in step 3006, the method 3000 may include computing one or more points of interest on the de-noised image. Computing one or more points of interest on the de-noised image may include: creating a search unit for searching the de-noised image; creating one or more search points on the de-noised image; and interpolating, for each search unit associated with a search point, pixel intensity from the de-noised image onto the search unit. The search unit may include a circle. Computing one or more points of interest on the de-noised image may also or instead include using a linear translation to shift the search unit in a two-dimensional coordinate plane. In an aspect, all local maxima within a breast mask of the de-noised image are used as search-points.

In an aspect, a point of interest included in the one or more points of interest satisfies each of the following conditions:

$$\frac{\langle I_{DN}(x_s(\theta), y_s(\theta)) \rangle}{\max(I_{DN}(x_s(\theta), y_s(\theta)))} < \tau_1,$$

and $$\frac{\langle I_{DN}(x_s(\theta), y_s(\theta)) \rangle}{I_0} > \tau_2$$

The point of interest may be at least a predetermined distance from a boundary of the breast. In an aspect, the predetermined distance is about 5 millimeters.

As shown in step 3008, the method 3000 may include creating one or more mesoscale regions of interest on the de-noised image. Creating the one or more mesoscale regions of interest may start in a corner of the de-noised image in a two-dimensional grid pattern with predetermined spacing along both an x-axis and a y-axis. The predetermined spacing may be about 1.3 millimeters. Each mesoscale region of interest may be contained within a breast mask of the de-noised image.

As shown in step 3010, the method 3000 may include computing a connectivity for each of the one or more mesoscale regions of interest. Computing the connectivity may include computing the points of interest included within a region of interest, computing a connectivity index for the region of interest, and recording neighbors connected to the region of interest. The connectivity index may include a number of non-empty neighbors connected to the region of interest.

As shown in step 3012, the method 3000 may include identifying one or more connected components using the computed connectivity, where each of the one or more connected components represents a branch of a global curvilinear structure. Each connected component may include a set of mesoscale regions of interest in which each region of interest contained therein has at least one nearest neighbor also contained in the set of mesoscale regions of interest and no nearest neighbor from a different set of mesoscale regions of interest.

The method 3000 may also or instead include computing one or more physical properties of one or more connected components. The method 3000 may also or instead include associating each of the one or more connected components with a connectivity ratio and a roundness ratio.

As shown in step 3014, the method 3000 may include selecting a set of branches based on one or more physical properties for each branch of the global curvilinear structure. The one or more physical properties may include a number of regions of interest included in a branch and a roundness ratio of the branch. The method 3000 may also or instead include discarding branches from the set of branches when the number of regions of interest is less than 4, when the number of regions of interest is 5 and the roundness ratio is greater than 12, when the number of regions of interest is 6 and the roundness ratio is greater than 14, when the number of regions of interest is 7 and the roundness ratio is greater than 20, or when the number of regions of interest is 8 and the roundness ratio is greater than 26.

The one or more physical properties may also or instead include a connectivity ratio and a roundness ratio of the branch. The method 3000 may also or instead include retaining branches when the connectivity ratio is less than or equal to a threshold value of connectivity and when the roundness ratio is greater than or equal to a threshold value for roundness. In an aspect, the threshold value of connectivity is about 5.69. In an aspect, the threshold value for roundness is about 1.49. In an aspect, each of the threshold value of connectivity and the threshold value for roundness is selected to favor long curvilinear structures.

Selecting the set of branches may also or instead include: discarding branches from the set of branches when a number of regions of interest is less than 4, when the number of regions of interest is 5 and a roundness ratio is greater than 12, when the number of regions of interest is 6 and the roundness ratio is greater than 14, when the number of regions of interest is 7 and the roundness ratio is greater than 20, or when the number of regions of interest is 8 and the roundness ratio is greater than 26; and retaining branches when a connectivity ratio is less than or equal to a threshold value of connectivity and when the roundness ratio is greater than or equal to a threshold value for roundness. The threshold value of connectivity may be about 5.69 and the threshold value for roundness may be about 1.49.

The method 3000 may also or instead include computing one or more physical properties of the mesoscale regions of interest. The method 3000 may also or instead include associating each region of interest by its mean brightness and a computed centroid location. The method 3000 may also or instead include replacing each region of interest with its computed centroid location.

As shown in step 3016, the method 3000 may include pruning each branch in the selected set of branches based on an error-tolerant, adaptive polynomial fit. Pruning each branch may include discarding points that are rejected by the error-tolerant, adaptive polynomial fit. The method 3000 may also or instead include discarding regions of interest and points of interest corresponding to the discarded points.

As shown in step 3018, the method 3000 may include identifying remaining regions of interest in each pruned branch. The method 3000 may also or instead include identifying remaining points of interest in the remaining regions of interest. The remaining points of interest may form a curvilinear structure representing one or more calcified arteries in the breast. The remaining points of interest may represent growth sites to which micro-calcifications may attach themselves in the breast. The remaining points of interest may represent a chain, where further growth occurs at endpoints of the chain.

The method 3000 may also or instead include detecting and selecting micro-calcifications based on one or more of a morphology, a topology, and a hierarchy of individual micro-structures. Detecting and selecting micro-calcifications may be further based on an inter-structure relationship of the individual micro-structures. Detecting and selecting micro-calcifications may include the use of a Q-algorithm.

As shown in step 3020, the method 3000 may include growing a chain formed by remaining points of interest included in the remaining regions of interest, where the chain represents a macroscopic, global curvilinear calcified arterial structure.

The method 3000 may also or instead include analyzing the chain. Analyzing the chain may include calculating further growth of the chain. The further growth may occur at endpoints of the chain.

The method 3000 may also or instead include applying growth repeatedly until saturation is achieved. Saturation may be achieved when a number of growth sites becomes unchanged with further attempts to grow the chain.

As shown in step 3022, the method 3000 may include applying the global curvilinear calcified arterial structure to a specific application—e.g., in predicting arterial calcifications in other tissues and subsequently developing a risk stratification prediction of disease based upon the arterial calcifications.

There exists a correlation between coronary artery calcium ("CAC"), heart disease and BAC. Matsumura, M E et al. Breast artery calcium noted on screening mammography is predictive of high risk coronary calcium in asymptomatic women: a case control study. Vasa. 2013 November; 42(6): 429-33. But there are instances wherein a patient may have a high CAC score that has no discernible BAC. However, so long as the presence of BAC correlates strongly with CAC score and the percentage of cases with no BAC but high CAC score is significantly smaller than the cases with BAC and high CAC score, one can improve the quantitation of heart disease by analyzing BAC.

The plan design is as follows:
1. Categorize the cases into 4 bins based on CAC scores.
2. Visually inspect all cases for the presence of any type of BAC, however, subtle they may be.
3. Assess the correlation and positive predictive value ("PPV") of BAC and CAC. The role of other variables (e.g., history of high cholesterol, diabetes, increasing age, smoking, hyperlipidemia, and family history of coronary artery disease) is also assessed such that together with the BAC, the presence may increase the correlation with CAC.
4. Optimize the correlation: Determining the difference between the type of BAC present in high CAC scores and the type of BAC present in low CAC scores enables one to develop a more accurate predictor of CAC based on the presence of BAC. To establish the difference, the following steps are taken: i) Create ground truths (GTs) for BACs in the two high CAC score category cases as well as GTs for BACs in the two low CAC score categories; ii) Build a deep learning based classifier to distinguish between the two categories of BAC; iii) Use the score from the classifier as the BAC score; and iv) Use this score as the indicator of BAC associated with CAC to determine the increase in PPV of BAC and CAC.

In an aspect, a method includes receiving a first image of a breast of a patient obtained during a mammogram, removing noise from the first image thereby creating a de-noised image, creating a search unit for searching the de-noised image, creating one or more search points on the de-noised image, interpolating, for each search unit associated with a search point, pixel intensity from the de-noised image onto the search unit, computing one or more points of interest on the de-noised image based on the interpolation, creating one or more mesoscale regions of interest on the de-noised image, and computing a connectivity for each of the one or more mesoscale regions of interest, where computing the connectivity includes computing points of interest included within a region of interest, computing a connectivity index for the region of interest, and recording neighbors connected to the region of interest. The method may also include identifying one or more connected components using the computed connectivity, where each connected component includes a set of mesoscale regions of interest in which each region of interest contained therein has at least one nearest neighbor also contained in the set of mesoscale regions of interest and no nearest neighbor from a different set of mesoscale regions of interest, and where each of the one or more connected components represents a branch of a global curvilinear structure. The method may further include computing one or more physical properties of the one or more connected components, selecting a set of branches based on the computed physical properties for each branch of the global curvilinear structure, pruning each branch in the selected set of branches based on an error-tolerant, adaptive polynomial fit, identifying remaining regions of interest in each pruned branch, identifying remaining points of interest in the remaining regions of interest, and growing a chain formed by the remaining points of interest, where the chain represents a macroscopic, global curvilinear calcified arterial structure.

In an aspect, a computer program product includes computer executable code embodied in a non-transitory computer readable medium that, when executing on one or more computing devices, performs the steps of: receiving a first image of a breast of a patient obtained during a mammogram, removing noise from the first image thereby creating a de-noised image, computing one or more points of interest on the de-noised image, creating one or more mesoscale regions of interest on the de-noised image, computing a connectivity for each of the one or more mesoscale regions of interest, and identifying one or more connected components using the computed connectivity, where each of the one or more connected components represents a branch of a global curvilinear structure. The computer program product may also include code that performs the steps of: selecting a set of branches based on one or more physical properties for each branch of the global curvilinear structure, pruning each branch in the selected set of branches based on an error-tolerant, adaptive polynomial fit, identifying remaining regions of interest in each pruned branch, and growing a chain formed by remaining points of interest included in the remaining regions of interest, where the chain represents a macroscopic, global curvilinear calcified arterial structure.

In an aspect, a computer program product includes computer executable code embodied in a non-transitory computer readable medium that, when executing on one or more computing devices, performs the steps of: receiving a first image of a breast of a patient obtained during a mammogram, removing noise from the first image thereby creating a de-noised image, creating a search unit for searching the de-noised image, creating one or more search points on the de-noised image, interpolating, for each search unit associated with a search point, pixel intensity from the de-noised image onto the search unit, computing one or more points of interest on the de-noised image based on the interpolation, creating one or more mesoscale regions of interest on the de-noised image, and computing a connectivity for each of the one or more mesoscale regions of interest, where computing the connectivity includes computing points of interest included within a region of interest, computing a connectivity index for the region of interest, and recording neighbors connected to the region of interest. The computer program product may also include code that performs the steps of: identifying one or more connected components using the computed connectivity, where each connected component includes a set of mesoscale regions of interest in which each region of interest contained therein has at least one nearest neighbor also contained in the set of mesoscale regions of interest and no nearest neighbor from a different set of mesoscale regions of interest, and where each of the one or more connected components represents a branch of a global curvilinear structure. The computer program product may further include code that performs the steps of: computing one or more physical properties of the one or more connected components, selecting a set of branches based on the computed physical properties for each branch of the global curvilinear structure, pruning each branch in the selected set of branches based on an error-tolerant, adaptive polynomial fit, identifying remaining regions of interest in each pruned branch, identifying remaining points of interest in the remaining regions of interest, and growing a chain formed by the remaining points of interest, where the chain represents a macroscopic, global curvilinear calcified arterial structure.

In an aspect, a system includes an imaging device (e.g., which may be one or more of the participants in the system shown in FIG. 1) and a computing device in communication with the imaging device (e.g., the computing device may be the computing device in the system shown in FIG. 1). The computing device may include a processor and a memory, where the memory bears computer executable code configured to perform the steps of: receiving a first image of a breast of a patient obtained during a mammogram, removing noise from the first image thereby creating a de-noised image, computing one or more points of interest on the de-noised image, creating one or more mesoscale regions of interest on the de-noised image, computing a connectivity for each of the one or more mesoscale regions of interest, and identifying one or more connected components using the computed connectivity, where each of the one or more connected components represents a branch of a global curvilinear structure. The memory may also bear computer executable code configured to perform the steps of: selecting a set of branches based on one or more physical properties for each branch of the global curvilinear structure, pruning each branch in the selected set of branches based on an error-tolerant, adaptive polynomial fit, identifying remaining regions of interest in each pruned branch, and growing a chain formed by remaining points of interest included in the remaining regions of interest, where the chain represents a macroscopic, global curvilinear calcified arterial structure.

In an aspect, a system includes an imaging device and a computing device in communication with the imaging device. The computing device may include a processor and a memory, where the memory bears computer executable code configured to perform the steps of: receiving a first image of a breast of a patient obtained during a mammogram, removing noise from the first image thereby creating a de-noised image, creating a search unit for searching the de-noised image, creating one or more search points on the de-noised image, interpolating, for each search unit associated with a search point, pixel intensity from the de-noised image onto the search unit, computing one or more points of interest on the de-noised image based on the interpolation, creating one or more mesoscale regions of interest on the de-noised image, and computing a connectivity for each of the one or more mesoscale regions of interest, where computing the connectivity includes computing points of interest included within a region of interest, computing a connectivity index for the region of interest, and recording neighbors connected to the region of interest. The memory may also bear computer executable code configured to perform the steps of: identifying one or more connected components using the computed connectivity, where each connected component includes a set of mesoscale regions of interest in which each region of interest contained therein has at least one nearest neighbor also contained in the set of mesoscale regions of interest and no nearest neighbor from a different set of mesoscale regions of interest, and where each of the one or more connected components represents a branch of a global curvilinear structure. The memory may further bear computer executable code configured to perform the steps of: computing one or more physical properties of the one or more connected components, selecting a set of branches based on the computed physical properties for each branch of the global curvilinear structure, pruning each branch in the selected set of branches based on an error-tolerant, adaptive polynomial fit, identifying remaining regions of interest in each pruned branch, identifying remaining points of interest in the remaining regions of interest, and growing a chain formed by the remaining points of interest, where the chain represents a macroscopic, global curvilinear calcified arterial structure.

In an aspect, a method of detecting and quantitating calcified arterial structures in breast tissue includes receiving a first image of a breast of a patient obtained during a mammogram, removing noise from the first image thereby creating a de-noised image, creating a search unit for searching the de-noised image, creating one or more search points on the de-noised image, interpolating, for each search unit associated with a search point, pixel intensity from the de-noised image onto the search unit, computing one or more points of interest on the de-noised image based on the interpolation, creating one or more mesoscale regions of interest on the de-noised image, and computing a connectivity for each of the one or more mesoscale regions of interest, where computing the connectivity includes computing points of interest included within a region of interest, computing a connectivity index for the region of interest, and recording neighbors connected to the region of interest. The method may also include identifying one or more connected components using the computed connectivity, where each connected component includes a set of mesoscale regions of interest in which each region of interest contained therein has at least one nearest neighbor also contained in the set of mesoscale regions of interest and no nearest neighbor from a different set of mesoscale regions of interest, and where each of the one or more connected components represents a branch of a global curvilinear structure. The method may further include computing one or more physical properties of the one or more connected components, selecting a set of branches based on the computed physical properties for each branch of the global curvilinear structure, pruning each branch in the selected set of branches based on an error-tolerant, adaptive polynomial fit, identifying remaining regions of interest in each pruned branch, identifying remaining points of interest in the remaining regions of interest, and growing a chain formed by the remaining points of interest, where the chain represents a macroscopic, global curvilinear calcified arterial structure. Further, the detected calcified arterial structures may be quantitated.

In an aspect, a method may include determining the risk of heart disease in a patient. Heart disease includes coronary heart disease or coronary artery disease. The method may include receiving a first image of a breast of a patient obtained during a mammogram, removing noise from the first image thereby creating a de-noised image, creating a search unit for searching the de-noised image, creating one or more search points on the de-noised image, interpolating, for each search unit associated with a search point, pixel intensity from the de-noised image onto the search unit, computing one or more points of interest on the de-noised image based on the interpolation, creating one or more mesoscale regions of interest on the de-noised image, and computing a connectivity for each of the one or more mesoscale regions of interest, where computing the connectivity includes computing points of interest included within a region of interest, computing a connectivity index for the region of interest, and recording neighbors connected to the region of interest. The method may also include identifying one or more connected components using the computed connectivity, where each connected component includes a set of mesoscale regions of interest in which each region of interest contained therein has at least one nearest neighbor also contained in the set of mesoscale regions of interest and no nearest neighbor from a different set of mesoscale regions of interest, and where each of the one or more connected components represents a branch of a global curvilinear structure. The method may further include computing one or more physical properties of the one or more connected components, selecting a set of branches based on the computed physical properties for each branch of the global curvilinear structure, pruning each branch in the selected set of branches based on an error-tolerant, adaptive polynomial fit, identifying remaining regions of interest in each pruned branch, identifying remaining points of interest in the remaining regions of interest, and growing a chain formed by the remaining points of interest, where the chain represents a macroscopic, global curvilinear calcified arterial structure. Further, the detected calcified arterial structures may be quantitated and the quantitated values for calcified arterial structures indicate the risk of heart disease.

Techniques thus may include a novel, easy-to-implement, and reliable technique to determine (calcified) global arterial structures.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

The systems and methods disclosed herein may be implemented via one or more components, systems, servers, appliances, other subcomponents, or distributed between such elements. When implemented as a system, such systems may include an/or involve, inter alia, components such as software modules, general-purpose CPU, RAM, etc., found in general-purpose computers. In implementations where the innovations reside on a server, such a server may include or involve components such as CPU, RAM, etc., such as those found in general-purpose computers.

Additionally, the systems and methods herein may be achieved via implementations with disparate or entirely different software, hardware and/or firmware components, beyond that set forth above. With regard to such other components (e.g., software, processing components, etc.) and/or computer-readable media associated with or embodying the present implementations, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the systems and methods may be achieved via or performed by logic and/or logic instructions including program modules, executed in association with such components or circuitry, for example. In general, program modules may include routines, programs, objects, components, data structures, etc., that perform particular tasks or implement particular instructions herein. The embodiments may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, where media of any type herein does not include transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the implementations described herein or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the implementations herein, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

Moreover, the above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method of determining risk of heart disease in a patient, the method comprising:
receiving a first image of a breast of the patient obtained during a mammogram;
removing noise from the first image thereby creating a de-noised image;
creating a search unit for searching the de-noised image, the search unit comprises predefined angular regions in a circle having a predefined radius;
creating one or more search points on the de-noised image, the one or more search points comprise one or more local maxima in brightness in the breast;
interpolating, for each search unit associated with a search point, pixel intensity from the de-noised image onto the search unit;
computing one or more points of interest on the de-noised image based on the interpolation;
creating one or more mesoscale regions of interest on the de-noised image;
computing a connectivity for each of the one or more mesoscale regions of interest, wherein computing the connectivity includes computing points of interest included within a region of interest, computing a connectivity index for the region of interest, and recording neighbors connected to the region of interest;
identifying one or more connected components using the computed connectivity, wherein each connected component includes a set of mesoscale regions of interest in which each region of interest contained therein has at least one nearest neighbor also contained in the set of mesoscale regions of interest and no nearest neighbor from a different set of mesoscale regions of interest, and wherein each of the one or more connected components represents a branch of a global curvilinear structure;
computing one or more physical properties of the one or more connected components;
selecting a set of branches based on the computed physical properties for each branch of the global curvilinear structure;
pruning each branch in the selected set of branches based on an error-tolerant, adaptive polynomial fit;
identifying remaining regions of interest in each pruned branch;
identifying remaining points of interest in the remaining regions of interest; and
growing a chain formed by the remaining points of interest, wherein the chain represents a macroscopic, global curvilinear calcified arterial structure,
wherein the detected calcified arterial structures are quantitated, and
wherein quantitated values for calcified arterial structures indicate risk of heart disease.

2. The method of claim 1, wherein the one or more physical properties include a number of regions of interest included in a branch and a roundness ration of the branch.

3. The method of claim 1, further comprising detecting and selecting micro-calcifications based on one or more of a morphology, a topology, and a hierarchy of individual micro-structures.

4. A system, comprising:
an imaging device; and
a computing device in communication with the imaging device, the computing device including a processor and a memory, the memory bearing computer executable code configured to perform the steps of:
receiving a first image of a breast of a patient obtained during a mammogram;
removing noise from the first image thereby creating a de-noised image;
creating a search unit for searching the de-noised image, the search unit comprises predefined angular regions in a circle having a predefined radius;
creating one or more search points on the de-noised image, the one or more search points comprise one or more local maxima in brightness in the breast;
interpolating, for each search unit associated with a search point, pixel intensity from the de-noised image onto the search unit;
computing one or more points of interest on the de-noised image based on the interpolation;
creating one or more mesoscale regions of interest on the de-noised image;
computing a connectivity for each of the one or more mesoscale regions of interest,
identifying one or more connected components using the computed connectivity, wherein each connected component represents a branch of a global curvilinear structure;
selecting a set of branches based on the computed physical properties for each branch of the global curvilinear structure;
pruning each branch in the selected set of branches based on an error-tolerant, adaptive polynomial fit;
identifying remaining regions of interest in each pruned branch; and
growing a chain formed by remaining points of interest included in the remaining regions of interest, wherein the chain represents a macroscopic, global curvilinear calcified arterial structure.

5. The system of claim 4, wherein the one or more physical properties include a number of regions of interest included in a branch and a roundness ratio of the branch.

6. The system of claim 4, wherein selecting the set of branches comprises:
discarding branches from the set of branches when a number of regions of interest is less than 4, when the number of regions of interest is 5 and a roundness ratio is greater than 12, when the number of regions of interest is 6 and a roundness ratio is greater than 14, when the number of regions of interest is 7 and a roundness ratio is greater than 20, or when the number of regions of interest is 8 and a roundness ratio is greater than 26; and
retaining branches when a connectivity ratio is less than or equal to a threshold value of connectivity and when the roundness ratio is greater than or equal to a threshold value for roundness.

7. The system of claim 4, wherein the computer executable code is further configured to perform the step of detecting and selecting micro-calcifications based on one or more of a morphology, a topology, and a hierarchy of individual micro-structures.

8. The system of claim 7, wherein detecting and selecting micro-calcifications is further based on an inter-structure relationship of the individual micro-structures.

9. The system of claim 8, wherein detecting and selecting micro-calcifications includes use of a Q-algorithm.

10. A computer program product comprising computer executable code embodied in a non-transitory computer readable medium that, when executing on one or more computing devices, performs the steps of:
- receiving a first image of a breast of a patient obtained during a mammogram;
- removing noise from the first image thereby creating a de-noised image;
- creating a search unit for searching the de-noised image, the search unit comprises predefined angular regions in a circle having a predefined radius;
- creating one or more search points on the de-noised image, the one or more search points comprise one or more local maxima in brightness in the breast;
- interpolating, for each search unit associated with a search point, pixel intensity from the de-noised image onto the search unit;
- computing one or more points of interest on the de-noised image based on the interpolation;
- creating one or more mesoscale regions of interest on the de-noised image;
- computing a connectivity for each of the one or more mesoscale regions of interest, identifying one or more connected components using the computed connectivity, wherein each connected component represents a branch of a global curvilinear structure;
- selecting a set of branches based on the computed physical properties for each branch of the global curvilinear structure;
- pruning each branch in the selected set of branches based on an error-tolerant, adaptive polynomial fit;
- identifying remaining regions of interest in each pruned branch; and
- growing a chain formed by remaining points of interest included in the remaining regions of interest, wherein the chain represents a macroscopic, global curvilinear calcified arterial structure.

11. The computer program product of claim 10, wherein the one or more physical properties include a number of regions of interest included in a branch and a roundness ratio of the branch.

12. The computer program product of claim 10, wherein selecting the set of branches comprises:
- discarding branches from the set of branches when a number of regions of interest is less than 4, when the number of regions of interest is 5 and a roundness ratio is greater than 12, when the number of regions of interest is 6 and a roundness ratio is greater than 14, when the number of regions of interest is 7 and a roundness ratio is greater than 20, or when the number of regions of interest is 8 and a roundness ratio is greater than 26; and
- retaining branches when a connectivity ratio is less than or equal to a threshold value of connectivity and when the roundness ratio is greater than or equal to a threshold value for roundness.

13. The computer program product of claim 10, further comprising code that performs the set of detecting and selecting micro-calcifications based on one or more of a morphology, a topology, and a hierarchy of individual micro-structures.

14. The computer program product of claim 10, wherein detecting and selecting micro-calcifications is further based on an inter-structure relationship of the individual micro-structures.

15. The computer program product of claim 14, wherein detecting and selecting micro-calcifications includes use of a Q-algorithm.

* * * * *